(12) United States Patent
Jimenez et al.

(10) Patent No.: US 7,703,163 B2
(45) Date of Patent: Apr. 27, 2010

(54) TOOTHBRUSH WITH ENHANCED CLEANING EFFECTS

(75) Inventors: Eduardo Jimenez, Manalapan, NJ (US); John J. Gatzemeyer, Hillsborough, NJ (US); Alan V. Sorrentino, Cranbury, NJ (US); Thomas Mintel, Rahway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/768,363

(22) Filed: Jan. 30, 2004

(65) Prior Publication Data

US 2005/0091769 A1    May 5, 2005

Related U.S. Application Data

(63) Continuation-in-part of application No. 10/697,213, filed on Oct. 30, 2003.

(51) Int. Cl.
*A46B 9/02* (2006.01)
*A61C 17/22* (2006.01)

(52) U.S. Cl. ............. 15/22.1; 15/167.1; 15/201

(58) Field of Classification Search ............. 15/22.1, 15/22.2, 110, 111, DIG. 5, DIG. 6, 167.1, 15/201
See application file for complete search history.

(56) References Cited

U.S. PATENT DOCUMENTS

| | | | | |
|---|---|---|---|---|
| 1,770,195 A | 7/1930 | Burlew | ............. | 15/167.1 |
| 2,244,098 A | 6/1941 | Busick | ............. | 15/172 |
| 2,263,802 A | 11/1941 | Grusin | | |
| 2,706,825 A | 4/1955 | Blakeman | ............. | 15/176.4 |
| 3,129,449 A | 4/1964 | Cyzer | | |
| 3,196,299 A * | 7/1965 | Kott | ............. | 310/81 |
| 3,316,576 A | 5/1967 | Urbush | ............. | 15/22.1 |
| 3,398,421 A | 8/1968 | Rashbaum | | |
| 4,114,222 A | 9/1978 | Serediuk | | |
| 4,654,922 A | 4/1987 | Chen | | |
| 4,694,844 A | 9/1987 | Berl et al. | | |
| 4,783,869 A | 11/1988 | Lee | ............. | 15/22.1 |
| 5,305,492 A * | 4/1994 | Giuliani et al. | ............. | 15/176.1 |
| 5,325,560 A | 7/1994 | Pavone et al. | | |

(Continued)

FOREIGN PATENT DOCUMENTS

DE    19817704 A1    10/1999

(Continued)

OTHER PUBLICATIONS

English translation of Abstract of JP 2002-10832, Suzuki, Jan. 2002.*

(Continued)

*Primary Examiner*—Laura C Guidotti
(74) *Attorney, Agent, or Firm*—Amy M. Fernandez

(57) ABSTRACT

A toothbrush is provided for cleaning and/or massaging of teeth and gums having a mechanical vibratory element and a head having cleaning/treating elements on a plurality of different types of cleaning areas which provide for an enhanced cleaning, scrubbing and massaging effect. The cleaning/treating elements have different physical characteristics so that in addition to providing a varied cleaning/treating effect from the cleaning/treating elements themselves there is enhanced treatment as a result of the movement of the cleaning/treating elements imparted by the mechanical vibratory device.

12 Claims, 20 Drawing Sheets

U.S. PATENT DOCUMENTS

| | | | | |
|---|---|---|---|---|
| 5,355,546 | A | | 10/1994 | Scheier et al. ............. 15/167.2 |
| 5,398,366 | A | | 3/1995 | Bradley |
| 5,481,775 | A | | 1/1996 | Gentile et al. ................ 15/22.1 |
| 5,483,722 | A | | 1/1996 | Scheier et al. ............. 15/167.2 |
| 5,491,866 | A | | 2/1996 | Simonds |
| 5,511,275 | A | | 4/1996 | Volpenhein et al. |
| 5,524,319 | A | | 6/1996 | Avidor |
| 5,528,786 | A | | 6/1996 | Porat et al. .................... 15/22.1 |
| 5,546,624 | A | | 8/1996 | Bock ........................... 15/22.1 |
| 5,625,916 | A | | 5/1997 | McDougall |
| 5,628,082 | A | * | 5/1997 | Moskovich .................. 15/110 |
| 5,630,244 | A | | 5/1997 | Chang |
| 5,651,158 | A | | 7/1997 | Halm ........................ 15/167.1 |
| 5,689,850 | A | * | 11/1997 | Shekalim .................... 15/22.1 |
| 5,813,079 | A | * | 9/1998 | Halm ........................ 15/167.1 |
| RE35,941 | E | | 11/1998 | Stansbury, Jr. ............... 15/22.2 |
| 5,839,149 | A | | 11/1998 | Scheier et al. ............. 15/167.2 |
| 5,946,759 | A | | 9/1999 | Cann |
| 5,970,564 | A | | 10/1999 | Inns et al. ..................... 15/201 |
| 5,987,688 | A | | 11/1999 | Roberts et al. |
| 5,991,959 | A | * | 11/1999 | Raven et al. .................. 15/201 |
| 6,000,083 | A | | 12/1999 | Blaustein et al. |
| 6,088,870 | A | | 7/2000 | Hohlbein .................... 15/167.1 |
| 6,141,817 | A | | 11/2000 | Dawson .................... 15/167.1 |
| 6,161,245 | A | | 12/2000 | Weihrauch ................... 15/201 |
| 6,178,582 | B1 | | 1/2001 | Halm ........................ 15/167.1 |
| 6,219,874 | B1 | | 4/2001 | van Gelder et al. ......... 15/167.1 |
| 6,276,021 | B1 | | 8/2001 | Hohlbein .................... 15/167.1 |
| 6,311,358 | B1 | | 11/2001 | Soetewey et al. ............. 15/110 |
| 6,311,360 | B1 | | 11/2001 | Lanvers ...................... 15/191.1 |
| 6,338,176 | B1 | | 1/2002 | Smith et al. ..................... 15/28 |
| 6,408,476 | B1 | | 6/2002 | Cann ........................ 15/167.1 |
| 6,553,604 | B1 | | 4/2003 | Braun et al. ............... 15/167.1 |
| 6,564,416 | B1 | | 5/2003 | Claire et al. ............... 15/167.1 |
| 6,641,764 | B2 | | 11/2003 | Lanvers |
| 6,802,097 | B2 | | 10/2004 | Hafliger et al. ............... 15/22.1 |
| 6,931,688 | B2 | | 8/2005 | Moskovich et al. |
| 2002/0120991 | A1 | * | 9/2002 | Cacka et al. .................. 15/22.1 |
| 2002/0124333 | A1 | | 9/2002 | Hafliger ...................... 15/22.1 |
| 2003/0159224 | A1 | | 8/2003 | Fischer et al. |
| 2003/0182744 | A1 | | 10/2003 | Fattori et al. .................. 15/22.1 |
| 2004/0134007 | A1 | * | 7/2004 | Davies ........................ 15/110 |
| 2004/0168269 | A1 | | 9/2004 | Kunita et al. |
| 2004/0177462 | A1 | | 9/2004 | Brown, Jr. et al. ......... 15/167.1 |
| 2004/0200016 | A1 | * | 10/2004 | Chan et al. .................... 15/22.1 |
| 2004/0255416 | A1 | * | 12/2004 | Hohlbein ..................... 15/106 |

FOREIGN PATENT DOCUMENTS

| | | | |
|---|---|---|---|
| EP | 0 613 636 | A1 | 9/1994 |
| EP | 1 350 442 | A1 | 10/2003 |
| FR | 38 440 | | 5/1930 |
| GB | 2371217 | A | 7/2002 |
| JP | 401214306 | A | 8/1989 |
| JP | 5-76416 | A | 3/1993 |
| JP | 408322641 | A | 12/1996 |
| JP | 2001-190333 | * | 7/2001 |
| JP | 2002-10832 | * | 1/2002 |
| WO | WO 03/037210 | A1 | 5/2003 |
| WO | WO 03/043459 | A2 | 5/2003 |
| WO | 2004082428 | | 9/2004 |
| WO | WO 2004/082428 | | 9/2004 |

OTHER PUBLICATIONS

Computer generated English translation of JP 2002-10832, Suzuki, Jan. 2002.*

Computer generated English translation of JP 2001-190333, Jul. 2001.*

* cited by examiner

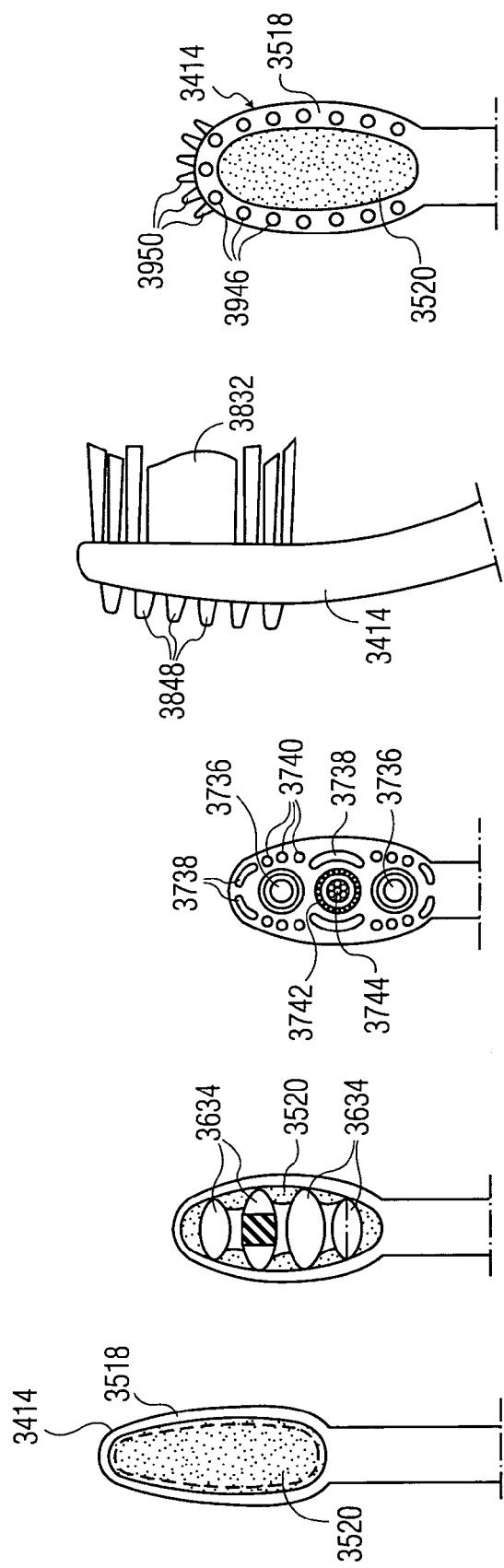

TOOTHBRUSH WITH ENHANCED CLEANING EFFECTS

RELATED APPLICATIONS

This application is a continuation-in-part application of U.S. application Ser. No. 10/697,213, filed on Oct. 30, 2003, the entirety of which is incorporated herein by reference.

FIELD OF THE INVENTION

The present invention relates to a toothbrush having a mechanical vibratory element and a head having different cleaning/treating elements attached thereon. The present invention also relates to manually held and operated toothbrushes having flexibly mounted bristles. The present invention further relates to a toothbrush, either manual or powered, which includes a handle and a head having elements mounted to the head such as tufts of bristles and/or elastomeric wipers.

Documents cited in this text, and all documents cited or referenced in the documents cited in this text, are incorporated herein by reference. Documents incorporated by reference into this text or any teachings therein may be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

BACKGROUND OF THE INVENTION

A powered toothbrush is designed to assist a user by mechanically moving the head of the toothbrush. One approach is to provide a vibratory element in the body of the toothbrush. U.S. Published Application No. 2002/0124333 relates to a mechanical vibratory device which causes the head part to vibrate. The vibratory device is accommodated in a front head part of the toothbrush, or in a neck-part region adjacent to the head part, said neck part connecting the head part to the handle, and is operatively connected to a power source, accommodated in the handle, via electrical connections running in the neck part, a vibration-dampening element preferably being provided in order to prevent vibration transmission to the handle, this achieves the situation where the vibrations which effect the improved cleaning action are produced predominantly in the head part and can only be felt to a slight extent in the handle, as a result of which comfortable handling of the toothbrush is achieved.

A number of approaches have been taken to provide flexibility to the bristles during use of a toothbrush. U.S. Pat. No. 5,970,564, for example, relates to a toothbrush having an elastomeric ridge wherein there is a center array of bristles and there is a side array of bristles mounted in elastomeric boots. A number of patents relate to a toothbrush head having sets of bristles, each of which is mounted to a non-rigid or elastic support element. Examples of these approaches are found in U.S. Pat. Nos. 1,770,195, 2,244,098, 6,161,245 and 6,311,360 and in French Patent No. 38440.

The head of a conventional toothbrush typically has a flat or slightly altered surface to which cleaning elements are attached. Usually the cleaning elements are strands of plastic material(s) formed into tufts, bundles or other groupings. A goal of many toothbrushes is to accommodate the cleaning element profile to that of the teeth being cleaned. Achieving that goal is complicated by the difficulty in matching a toothbrush profile to the complex surface of a typical set of human teeth. The latter generally lie in a "C" shaped curve which presents the need for a brush to address a convex outer curve and a concave inner curve. In addition, the toothbrush should be capable of cleaning irregularities on the tooth surface as well as the interproximal area between teeth.

It is well known that the ideal brushing technique from a dental hygiene perspective is an up and down stroke along the vertical surface of teeth which massages the gums while cleaning the teeth. However, due to a number of factors, including ergonomic difficulties, haste, lack of education or the like, few consumers use the recommended brushing technique. Rather, the typical consumer brushes across their teeth in a horizontal motion rather than a vertical movement. Various approaches have been taken by others to translate horizontal brush movement into partial vertical movement of the bristles or cleaning elements.

U.S. Pat. No. 4,783,869 relates to translation of horizontal to vertical movement of cleaning elements through use of a helix groove in a movable shaft within a toothbrush handle. The groove receives a pin which rides in the groove. This mechanism causes the toothbrush head to partially rotate or oscillate as the handle moves left-to-right or vice versa in the user's mouth. That rotation or oscillation causes the cleaning elements to move in a vertical plane perpendicular to movement of the toothbrush handle.

Other mechanisms for movement include an arcuate shaped base for a toothbrush head aligned with the longitudinal axis of the head, wherein a movable arcuate block having cleaning elements is flexibly mounted on the toothbrush head such that the block is free to slide on the head in a manner whereby the cleaning elements may travel in a vertical direction generally transverse to the typical side-to-side motion of the toothbrush; and a pivotal mounting of cleaning elements allowing for the elements to move up and down in concert with a side-to-side stroke along the teeth;

A toothbrush head should provide both proper support for the bristles, and be flexible enough during use to allow the bristles to conform to the shape of a user's mouth or teeth. Additionally, construction techniques should be inexpensive, versatile and consistent.

In an attempt to meet these criteria, a process known as "Anchor Free Tufting" ("AFT") has been used in the formation of toothbrush heads. In such an AFT process, a head plate for holding toothbrush bristles, and for eventual insertion into a toothbrush body, is typically formed of a rigid plastic that is conducive to sonic welding. The head plate is formed with a solid perimeter and defines a field of variously shaped and sized holes within this perimeter. Fibers that are to form the tufts are then placed in the holes in the field of the head plate, and the backs of the tufts are melted together to fix their position relative to one another.

The tufted head plate is then inserted into a predefined receiving portion of the head portion of a toothbrush handle and is sonically welded into place. The brush is then end-rounded and packaged for sale as a traditional toothbrush.

However, this manufacturing process results in a toothbrush with a very rigid head that does not easily conform to the physical characteristics of a user when brushing. Therefore, it would be desirable to provide a toothbrush that can be conveniently manufactured by the above process, but provides the desired flexibility of the head of the toothbrush during use.

It would also be desirable if a toothbrush could be provided having various cleaning/treating elements on a head, such as bristles with different degrees of flexible mounting, to have a enhanced cleaning effect when moved by a mechanical vibratory element.

Further, there is a continuing need in the art for new combinations and arrangements of bristle tufts to provide improved stiffness to enhanced plaque and debris removal, especially within interproximal spaces.

SUMMARY OF THE INVENTION

In accordance with one embodiment of the invention, a toothbrush is provided having a handle, a cleaning head attached to said handle, and a mechanical vibratory device which causes the cleaning head to vibrate, said mechanical vibratory device located in the cleaning head or in a region adjacent to the cleaning head and operatively connected to an electric power source, said cleaning head having an outer surface, said cleaning head including a frame, a resilient membrane secured across said frame and movable in a direction toward and away from said outer surface, said resilient membrane defining a cleaning field, a plurality of cleaning/treating elements mounted to said membrane in said cleaning field, at least some of said cleaning/treating elements having physical characteristics which differ from other of said cleaning/treating elements.

In accordance with another embodiment of the invention, a toothbrush is provided having an elongated member having a head at one end and a handle at the other end; and a mechanical vibratory device which causes the head to vibrate, said mechanical vibratory device located in the head or in a region adjacent to the cleaning head and operatively connected to an electric power source, wherein said head is comprised of a face with a peripheral portion about its exterior and an internal portion adjacent thereto, wherein said peripheral portion is comprised of a plurality of peripheral bristle tufts extending therefrom, and wherein said internal portion is comprised of a plurality of bristle bars extending therefrom.

In accordance with a further embodiment of the invention, a toothbrush is provided having a handle, a cleaning head attached to said handle, and a mechanical vibratory device which causes the cleaning head to vibrate, said cleaning head having an outer surface, and a plurality of cleaning/treating elements mounted to said outer surface, wherein at least some of said cleaning/treating elements having physical characteristics which differ from other of said cleaning/treating elements.

BRIEF DESCRIPTION OF THE DRAWINGS

In this specification and the accompanying drawings, some preferred embodiments of the invention are shown and described, and various alternatives and modifications thereof have been suggested. It is to be understood that these are not intended to be exhaustive and that many other changes and modifications can be made within the scope of the invention.

The suggestions herein are selected and included for purposes of illustration in order that others skilled in the art will more fully understand the invention and the principles thereof and will thus be enabled to modify it in a variety of forms, each as may be best suited to the conditions of a particular use.

Figure 1:
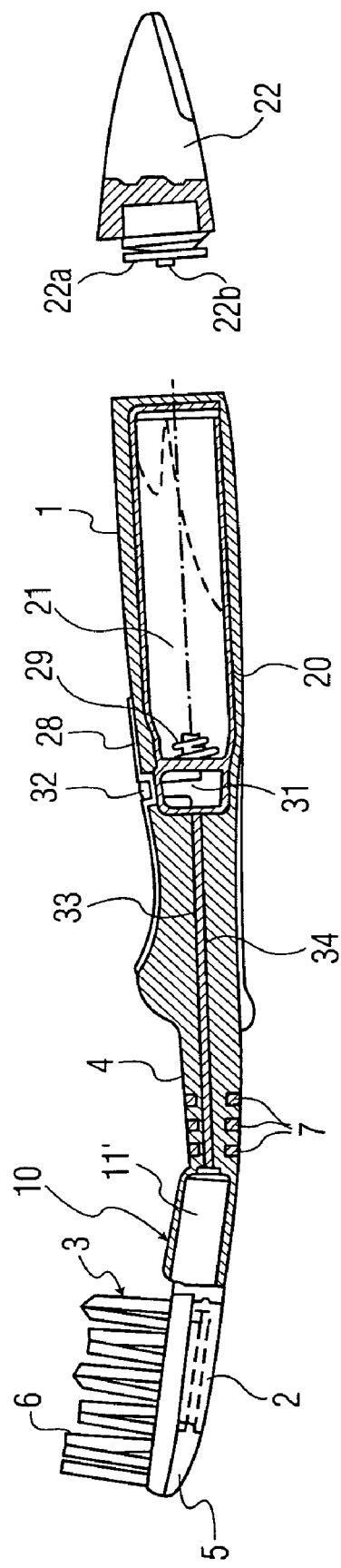

In the following detailed description, reference will be made to the accompanying drawings, wherein:

FIG. 1 shows a side view, partially in section, of a first exemplary embodiment of a toothbrush according to the invention and of a handle-closure part separated from one another (without a battery).

Figure 2:
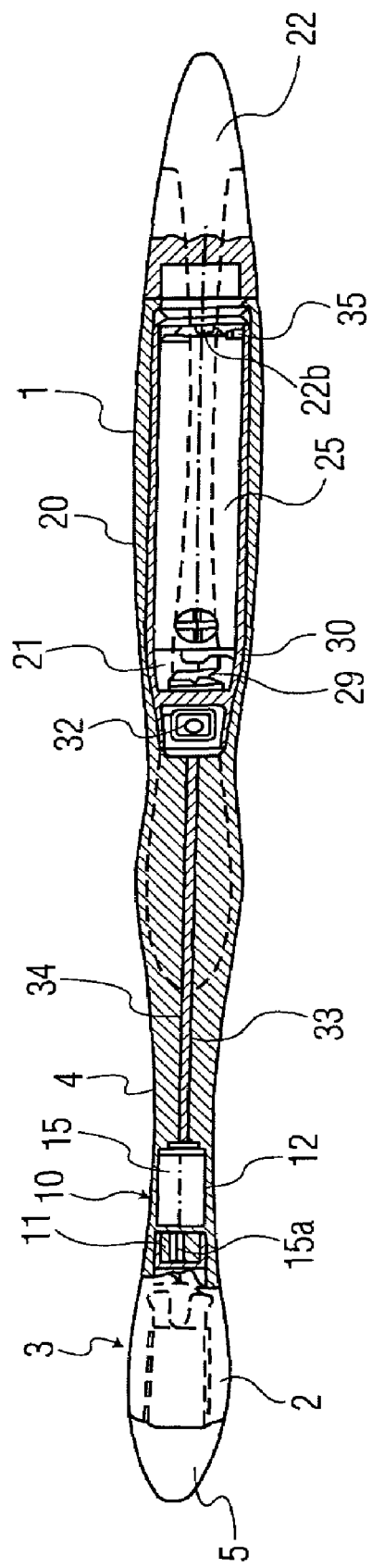

FIG. 2 shows a bottom view, partially in section, of a second exemplary embodiment of a toothbrush according to the invention in the assembled state.

Figure 3:
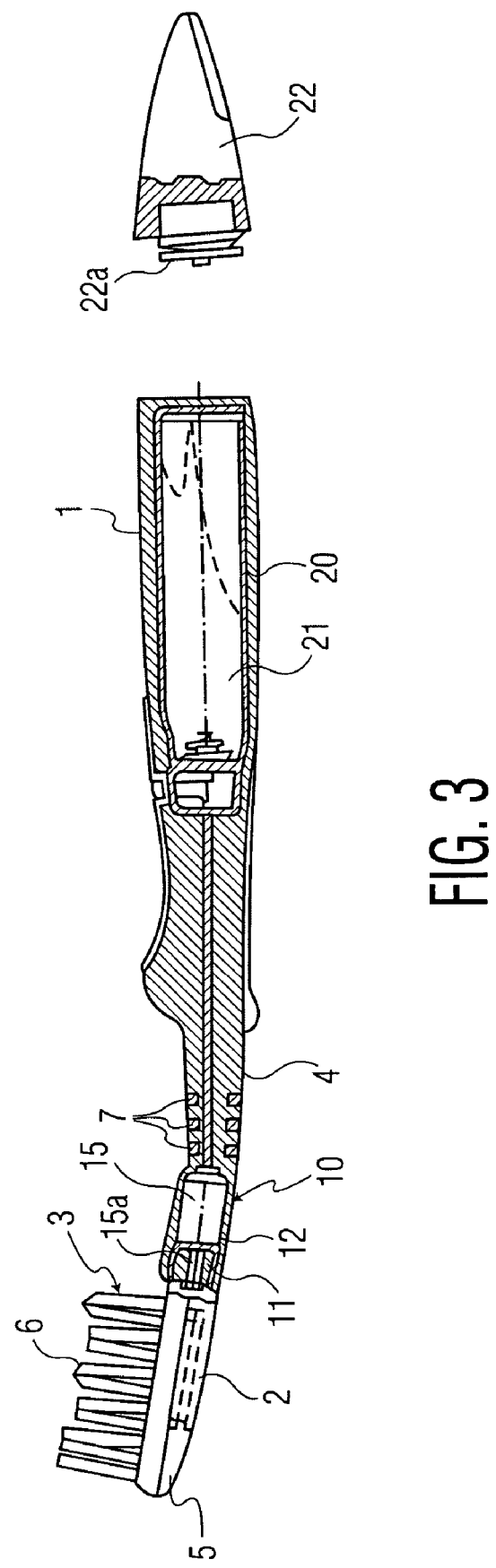

FIG. 3 shows a side view, partially in section, of the toothbrush according to FIG. 2 and the closure part separated from one another (without a battery).

Figure 4:
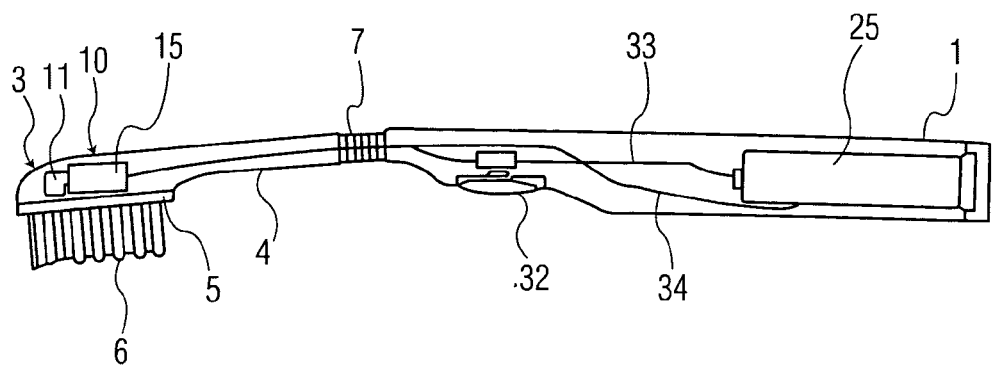

FIG. 4 shows a side view of a third exemplary embodiment of a toothbrush according to the invention in the assembled state.

Figure 5:
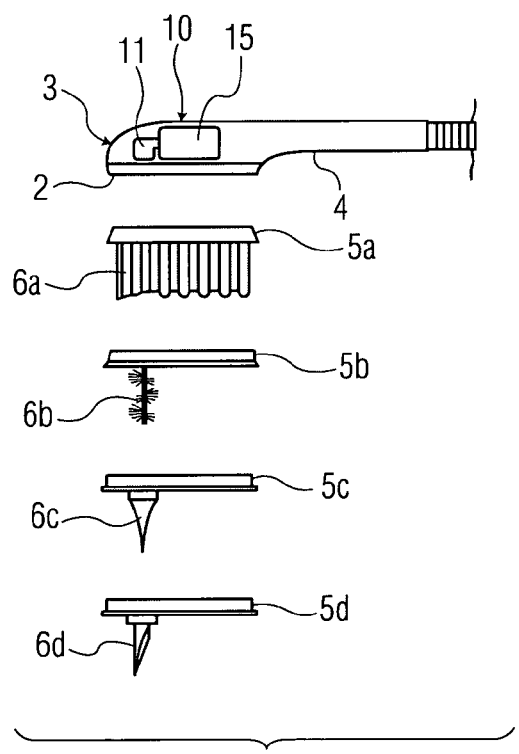

FIG. 5 shows a front part of the toothbrush according to FIG. 4 with different embodiments of exchangeable treatment heads.

Figure 6:
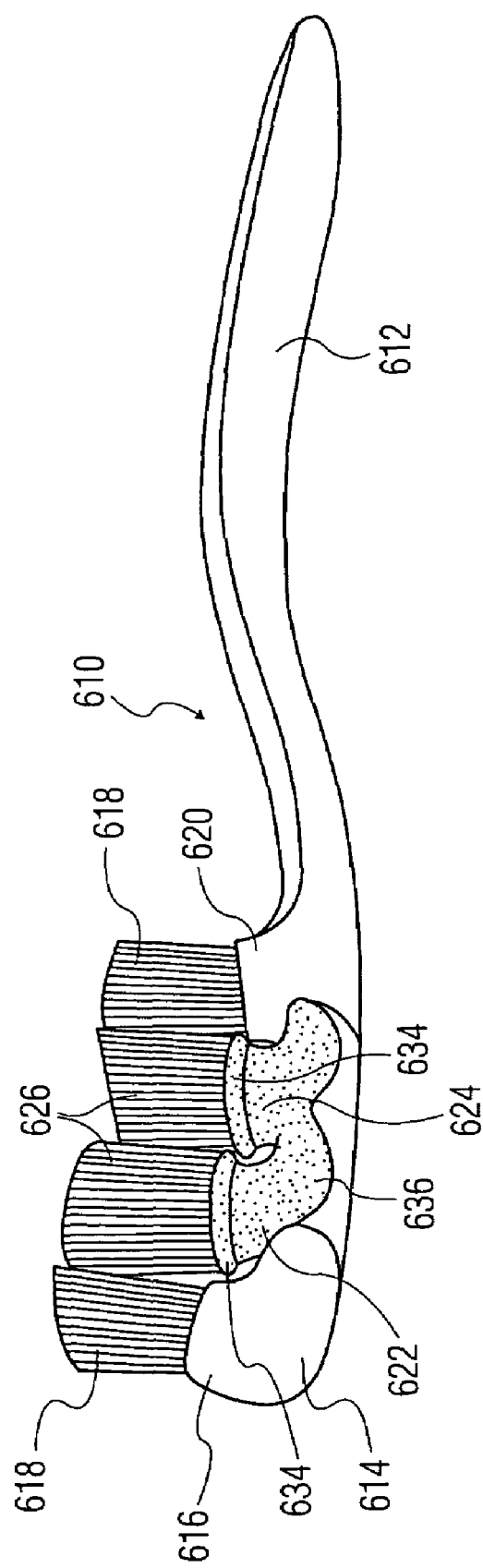

FIG. 6 is a perspective view of a toothbrush in accordance with this invention.

Figure 7:

FIG. 7 is a side elevational view of the toothbrush shown in FIG. 6.

Figure 8:
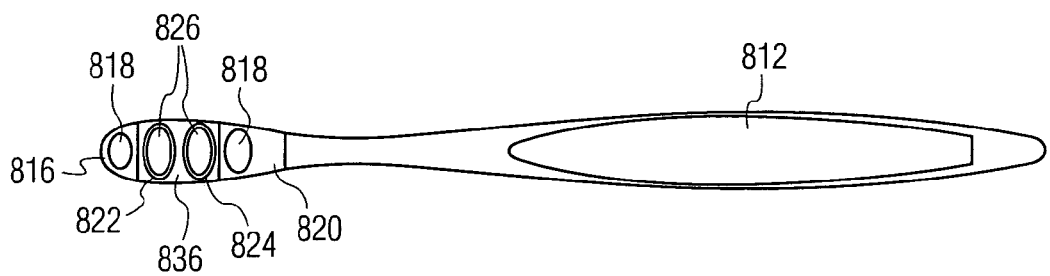

FIG. 8 is a front elevational view of the toothbrush shown in FIGS. 6-7.

Figure 9:
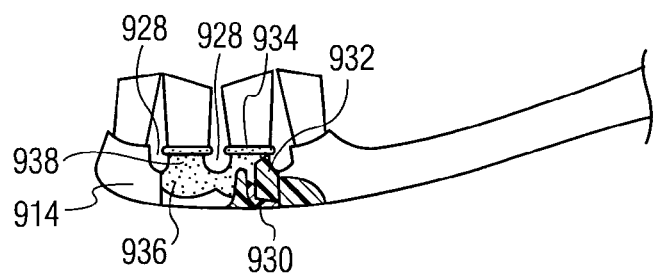

FIG. 9 is a side elevational view similar to FIG. 7 partially broken away.

Figure 10:
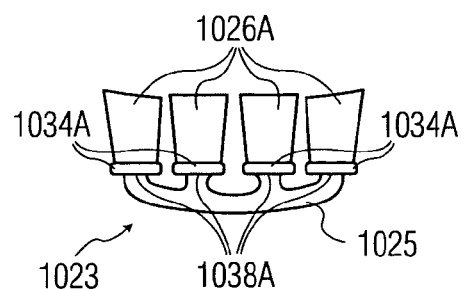

FIG. 10 is a side elevational view showing a subassembly of the bristle containing portion of the brush head in accordance with another aspect of this invention.

Figure 11:
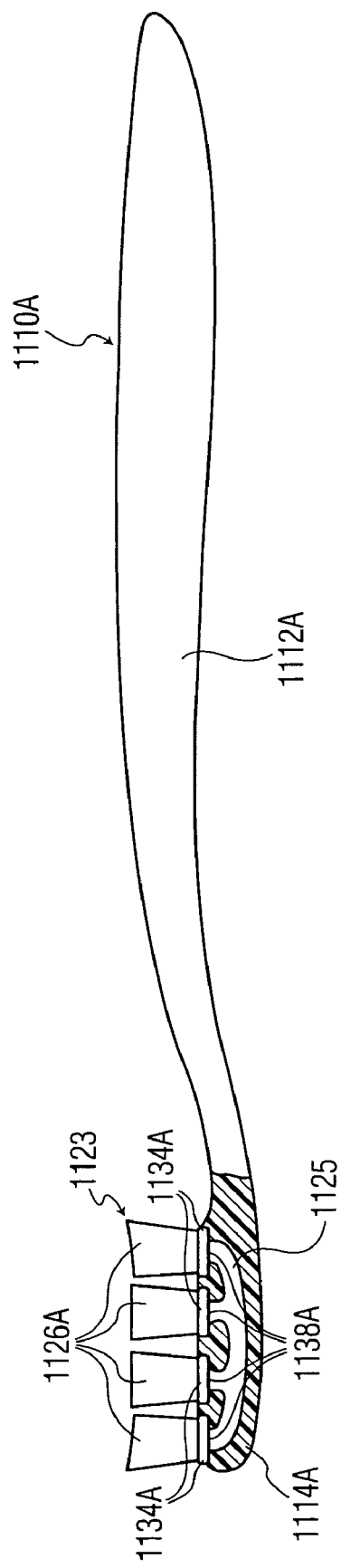

FIG. 11 is a side elevational view showing the subassembly of FIG. 10 incorporated in a completed toothbrush.

Figure 12:
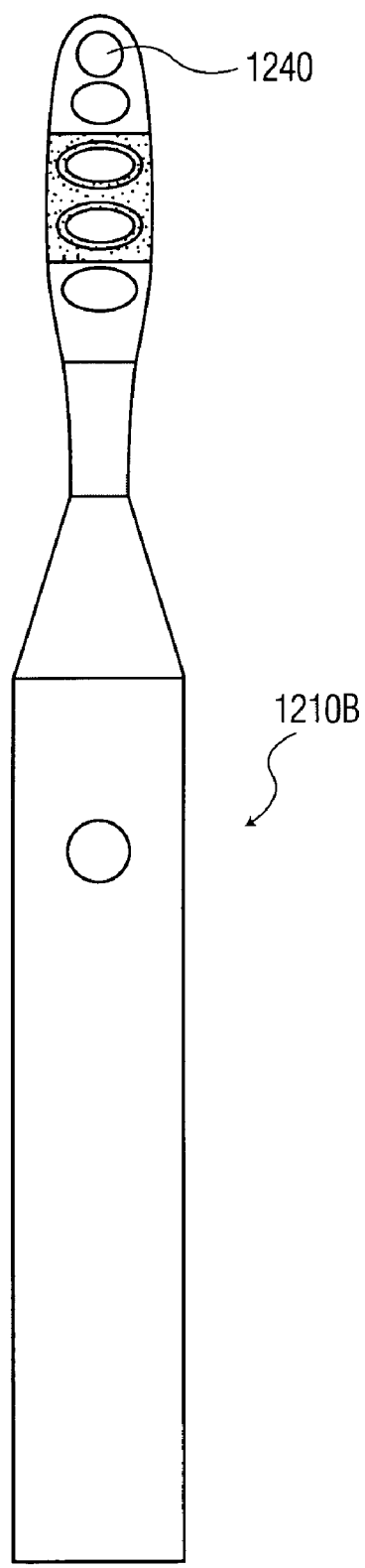

FIG. 12 is a front elevational view of a further toothbrush in accordance with this invention.

Figure 13:
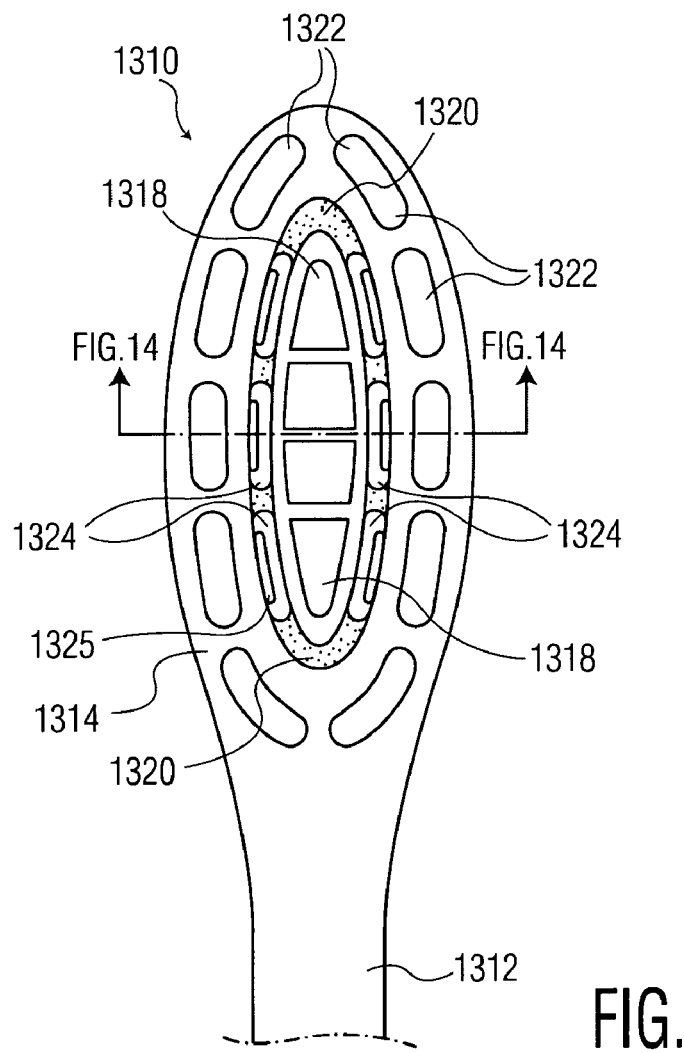

FIG. 13 is a top plan view of a manual toothbrush in accordance with this invention.

Figure 14:
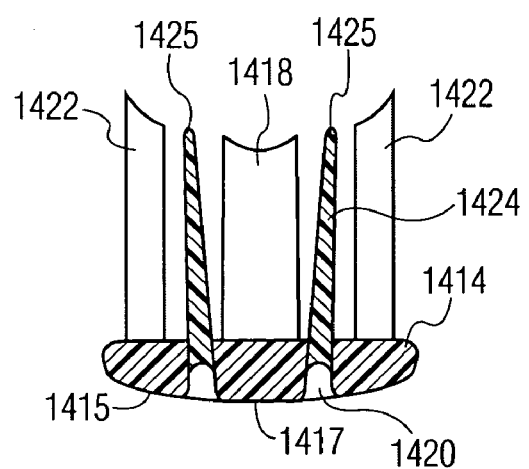

FIG. 14 is a side cross-sectional view taken along lines 14-14 of FIG. 12 showing the bristle and wiper arrangement with minimal force applied to the toothbrush handle.

Figure 15:
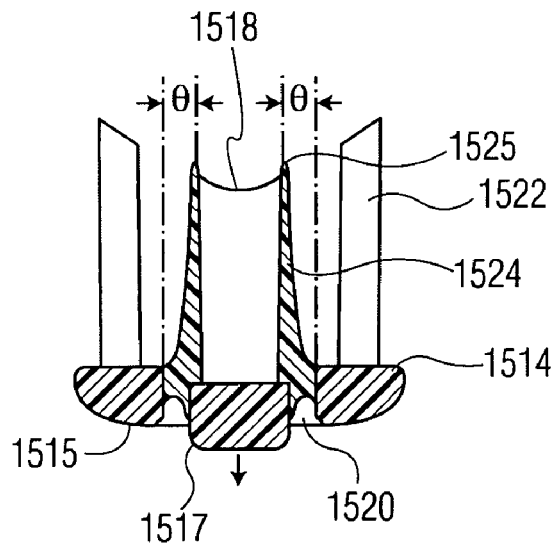

FIG. 15 is a side cross-sectional view taken along lines 14-14 of FIG. 12 showing the bristle and wiper arrangement where greater force is applied to the toothbrush handle.

Figure 16:
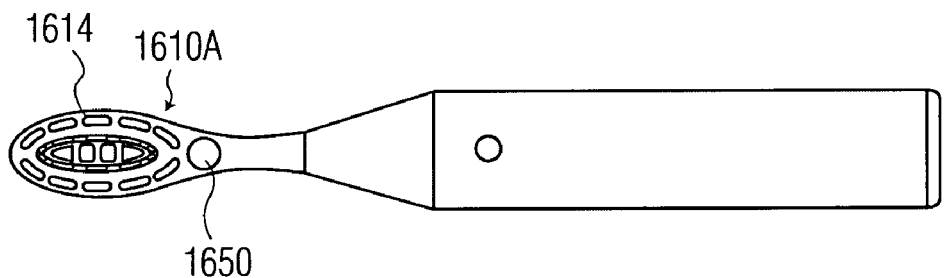

FIG. 16 is a top plan view of a powered toothbrush in accordance with this invention.

Figure 17:
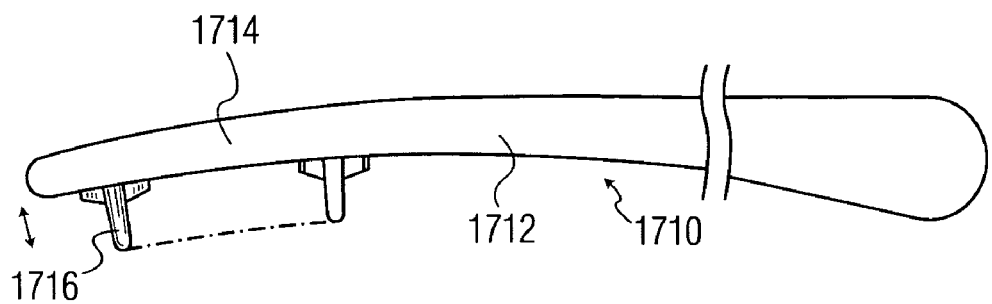

FIG. 17 is a side elevational overview of a toothbrush broken along its length having a flexible head with fingers mounted thereon, showing the ribs interconnecting the finger and flexible head.

Figure 18:
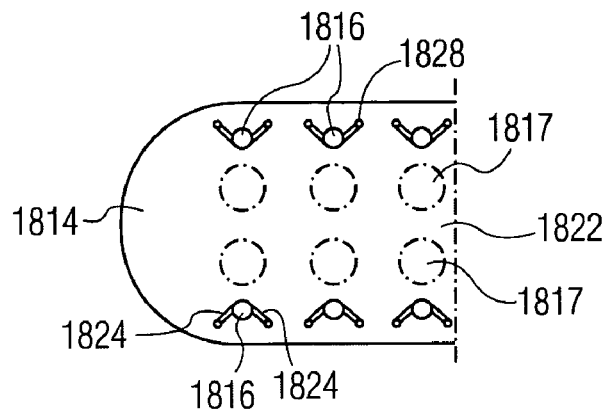

FIG. 18 is a fragmental front plan view showing an arrangement of fingers connected by ribs to a flexible head.

Figure 19:
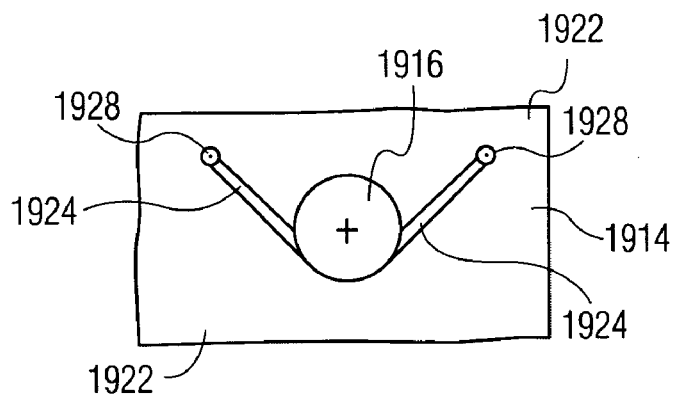

FIG. 19 is a fragmental plan view of single finger connected by ribs to an unflexed toothbrush head.

Figure 20:
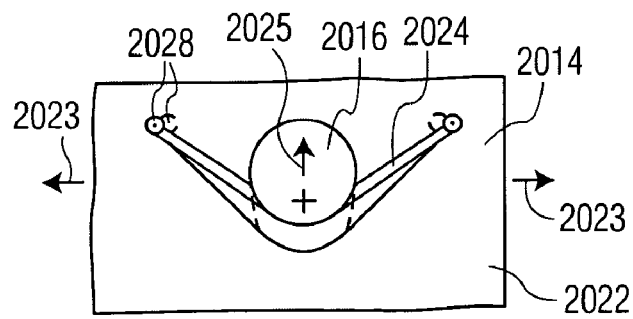
Figure 21:
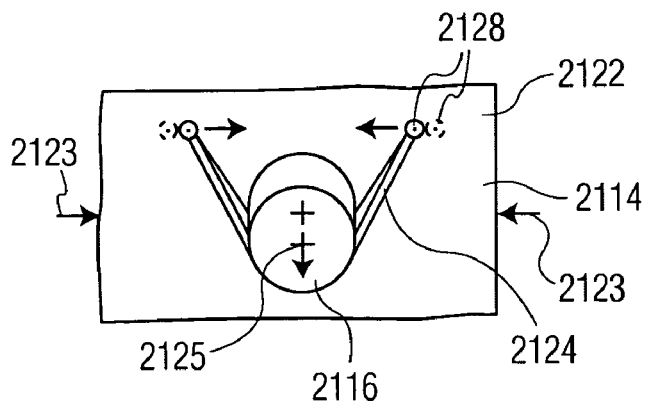

FIGS. 20 and 21 are fragmental plan views of a single finger connected by ribs to a flexible head in flexed positions caused by movement of the flexible head.

Figure 22:
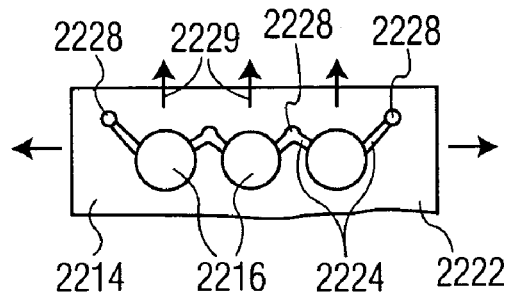
Figure 23:
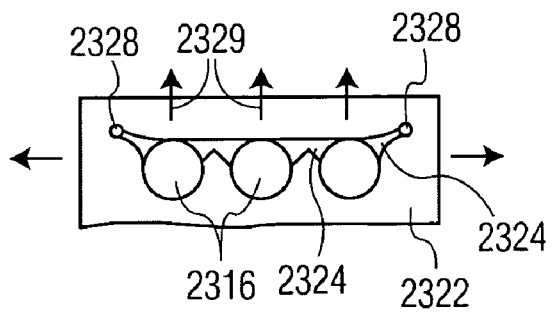
Figure 24:
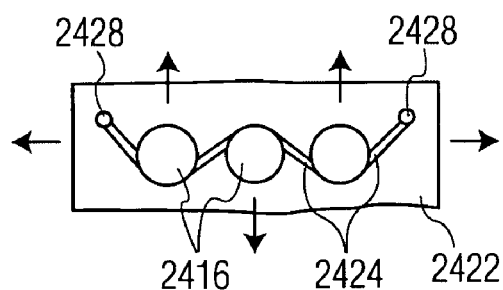

FIG. 22-24 are fragmental plan views of multiple fingers interconnected to each other and to a flexible toothbrush head by ribs forming a web between the fingers.

Figure 25:
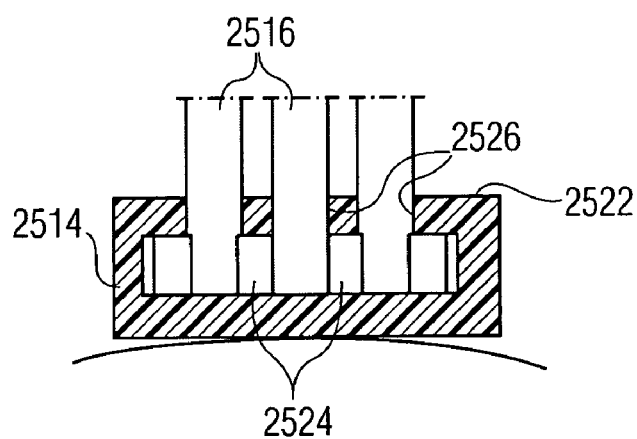

FIG. 25 is a fragmental cross-sectional view in elevation of the fingers mounted in a flexible toothbrush head.

Figure 26:
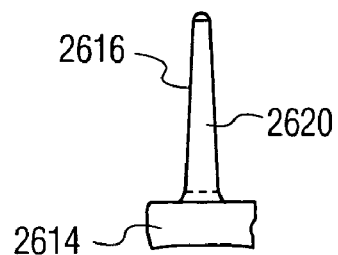
Figure 27:
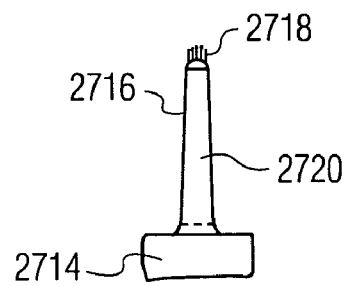
Figure 28:
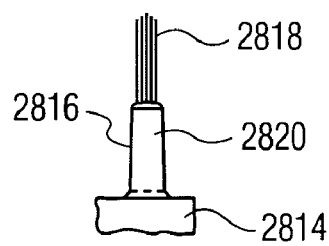

FIGS. 26-28 are fragmental elevational views of the fingers used with the toothbrush of the invention.

Figure 29:
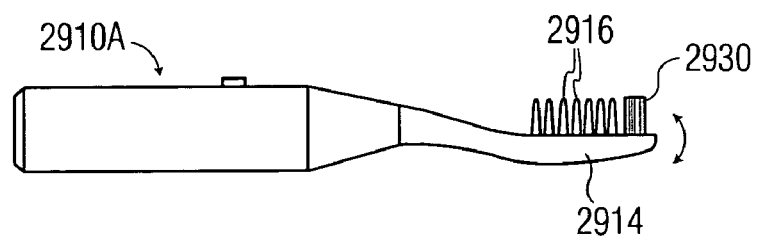

FIG. 29 is a side elevational view of a further toothbrush using a flexible head and gum stimulation fingers.

Figure 30:
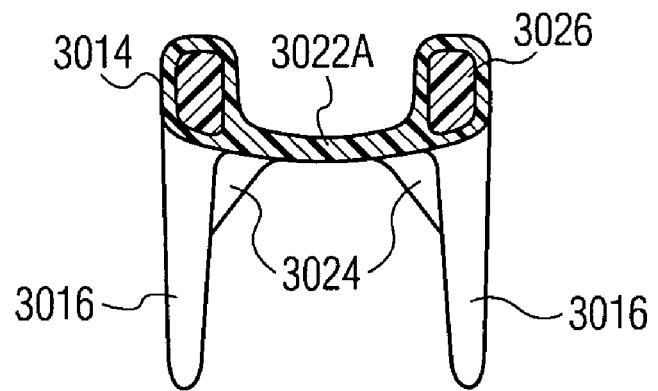
Figure 31:
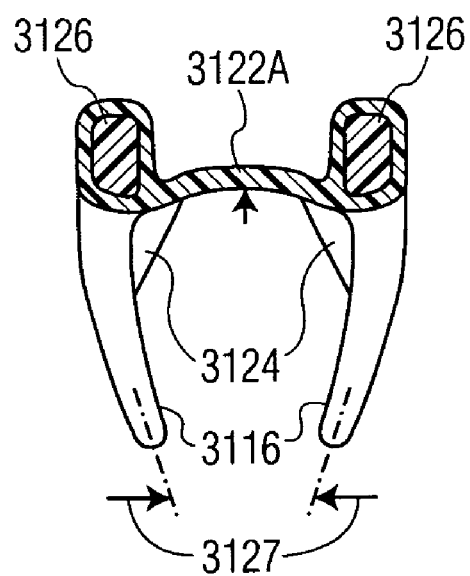

FIGS. 30 and 31 are cross sectional views of the fingers with ribs interconnecting the fingers to a flexible portion of the toothbrush head.

Figure 32:
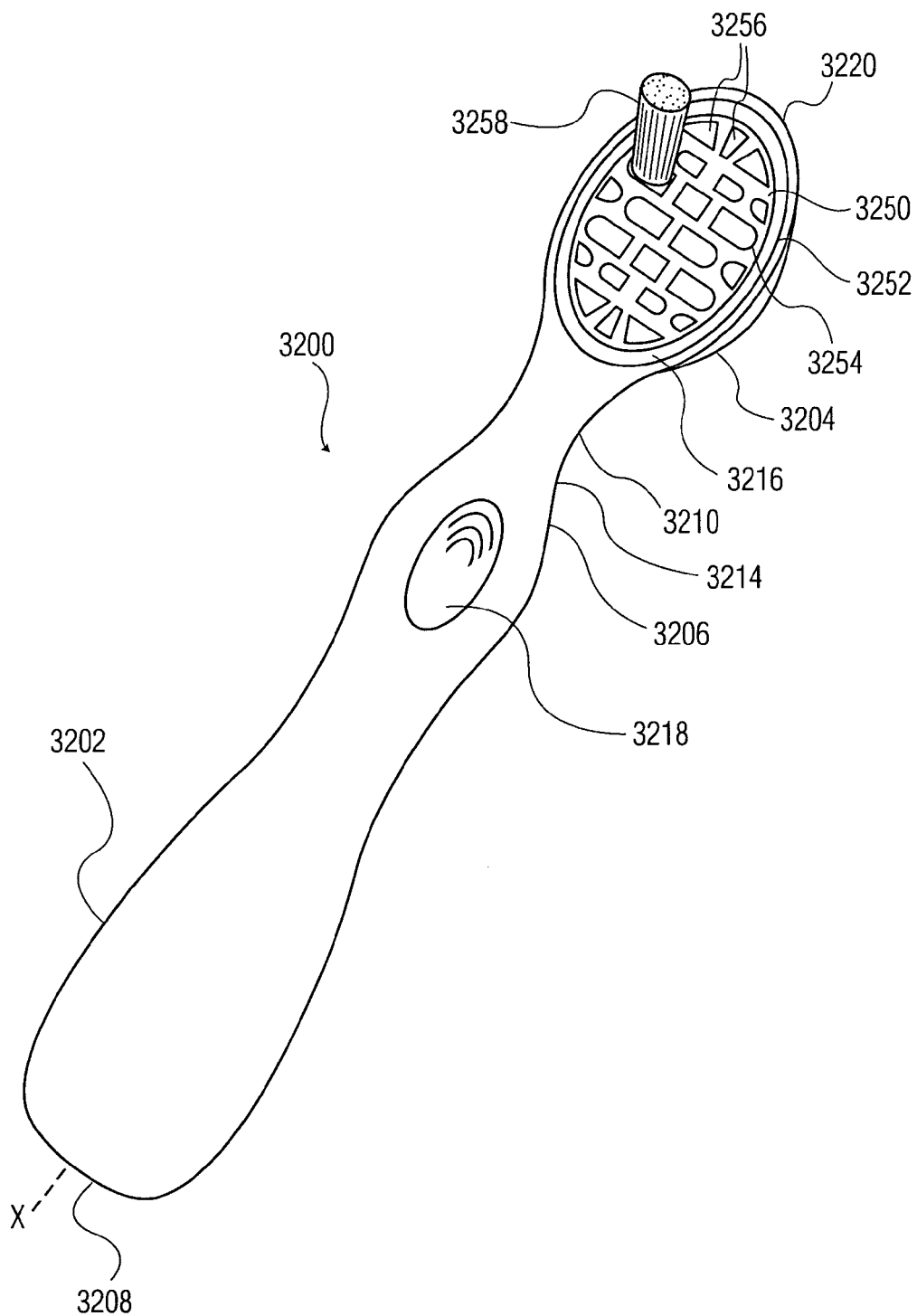

FIG. 32 is a perspective view of a toothbrush including a head constructed in accordance with a preferred embodiment of the invention.

Figure 33:
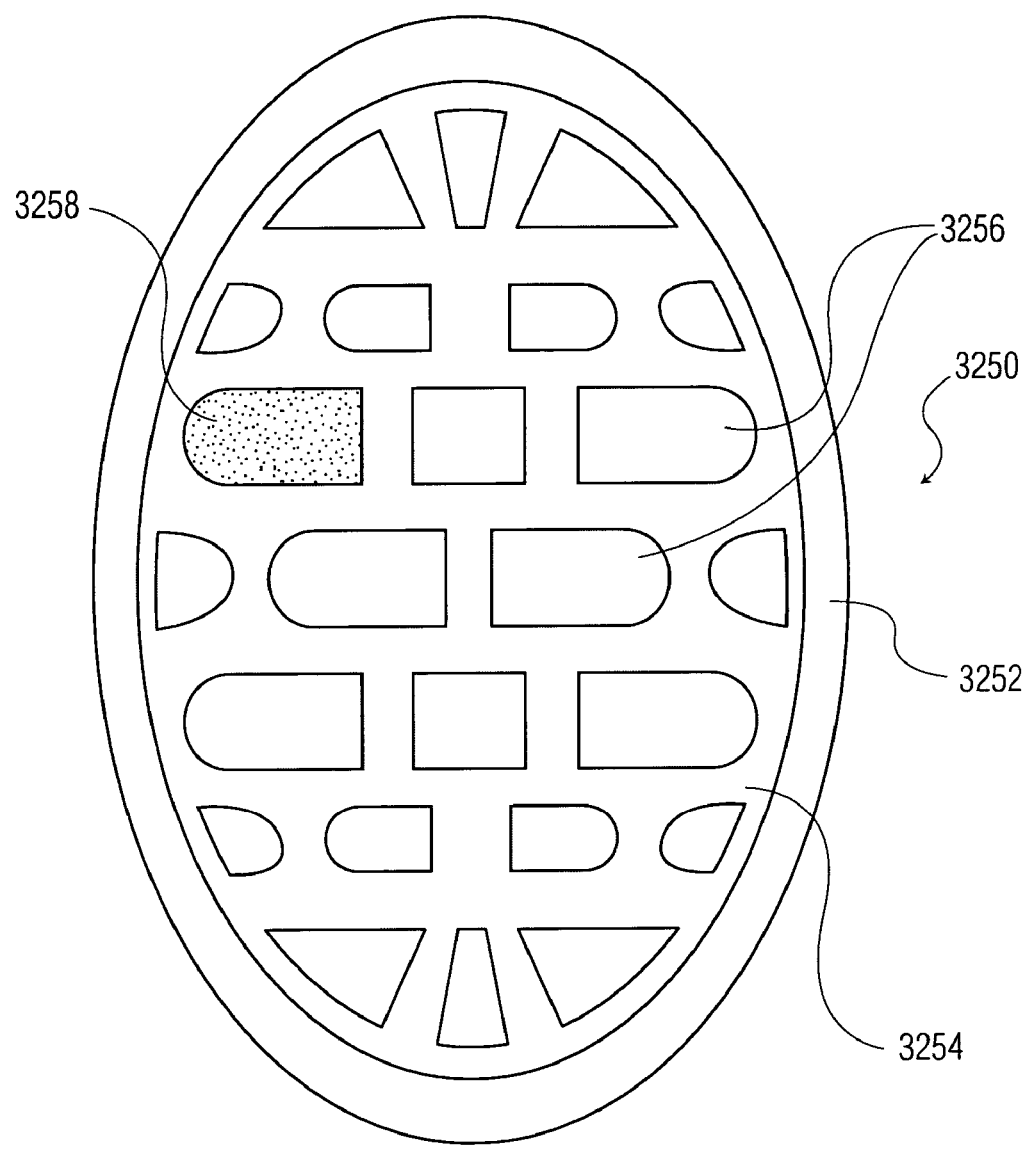

FIG. 33 is a top plan view of the head of FIG. 32.

Figure 34:
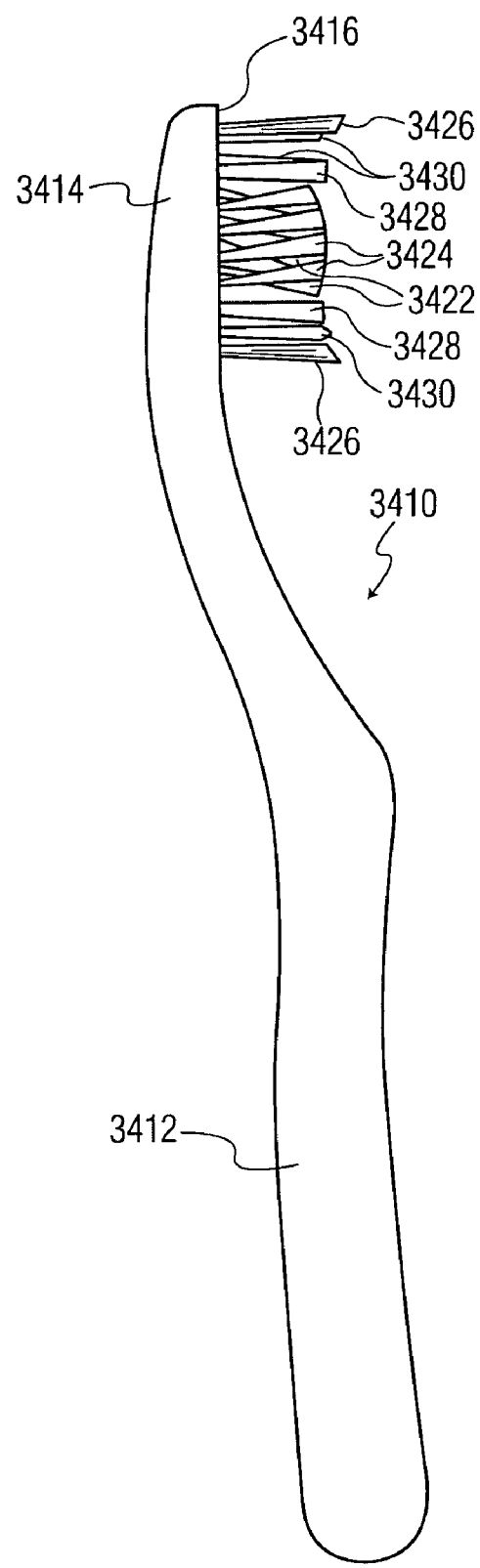

FIG. 34 is a side elevational view of a toothbrush in accordance with this invention.

FIG. 35 is a front elevational view showing the resilient cleaning field to which the cleaning/treating elements of FIG. 34 would be mounted.

FIGS. 36-37 are front elevational views of different forms of cleaning heads incorporating various cleaning/treating elements in the cleaning field.

FIG. 38 is a side elevational view of still yet another form of cleaning head in accordance with this invention.

FIG. 39 is a front elevational view similar to FIG. 35 of a modified form of cleaning head.

Figure 40:
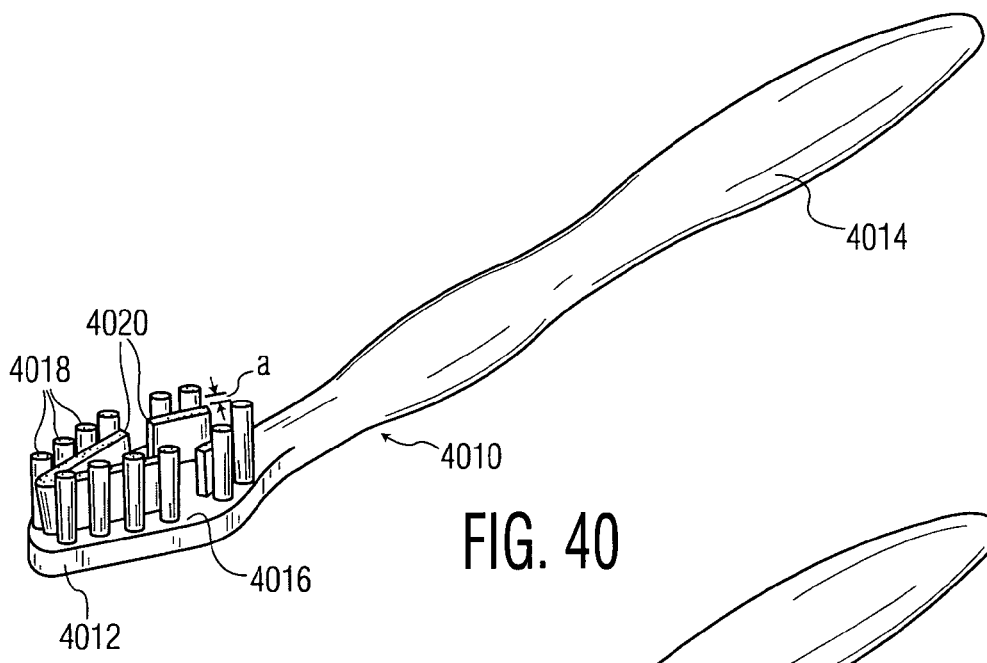

FIG. 40 is a perspective view of a first embodiment of a toothbrush of the present invention; wherein the bristle bars are generally in the form of parallelepipeds.

Figure 41:
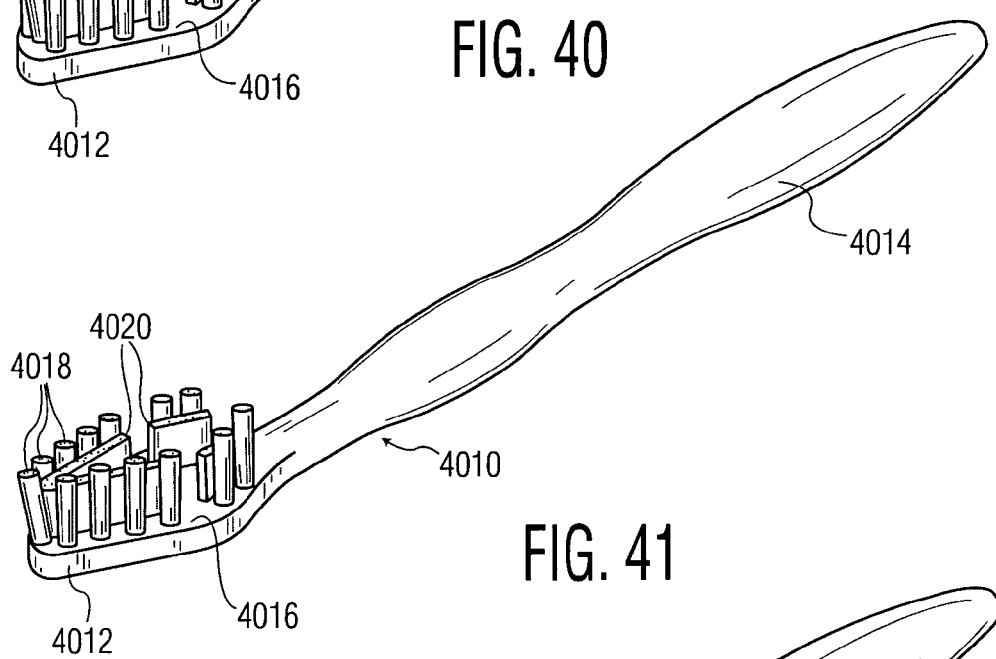

FIG. 41 is a perspective view of a second embodiment of a toothbrush of the present invention; wherein the bristle bars have generally curved foot-prints.

Figure 42:
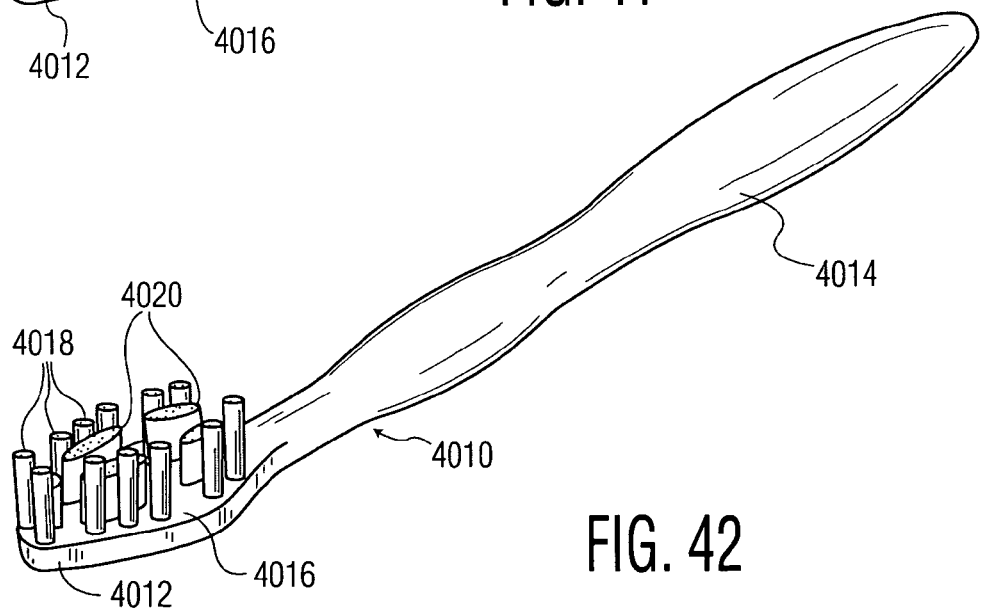

FIG. 42 is a perspective view of a third embodiment of a toothbrush of the present invention; wherein the bristle bars have generally oval footprints.

Figure 43:
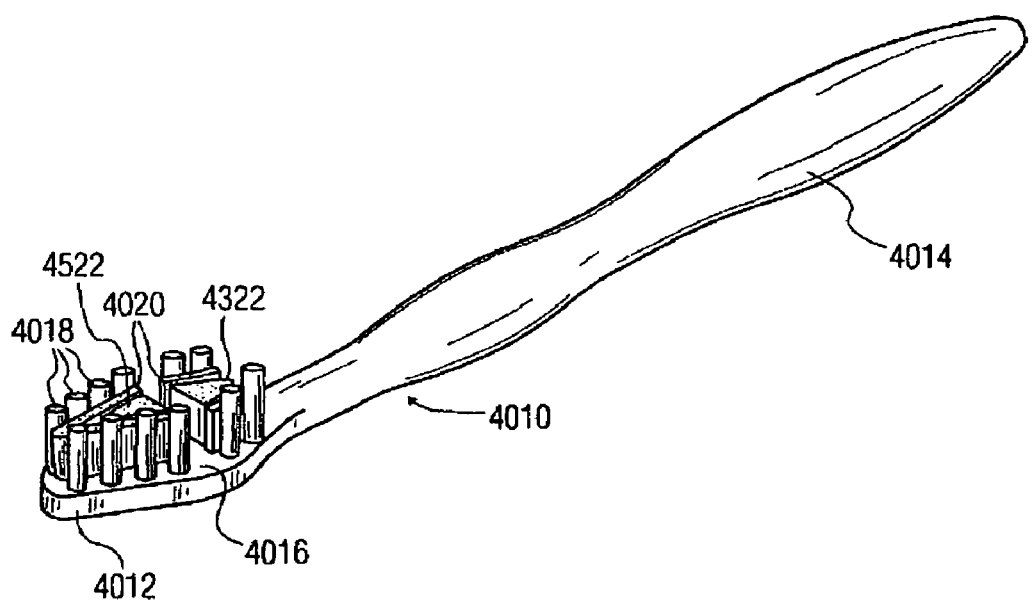

FIG. 43 is a perspective view of a fourth and alternative embodiment of the toothbrush shown in FIG. 40, wherein there are additional bristle bars located central to the toothbrush head.

Figure 44:
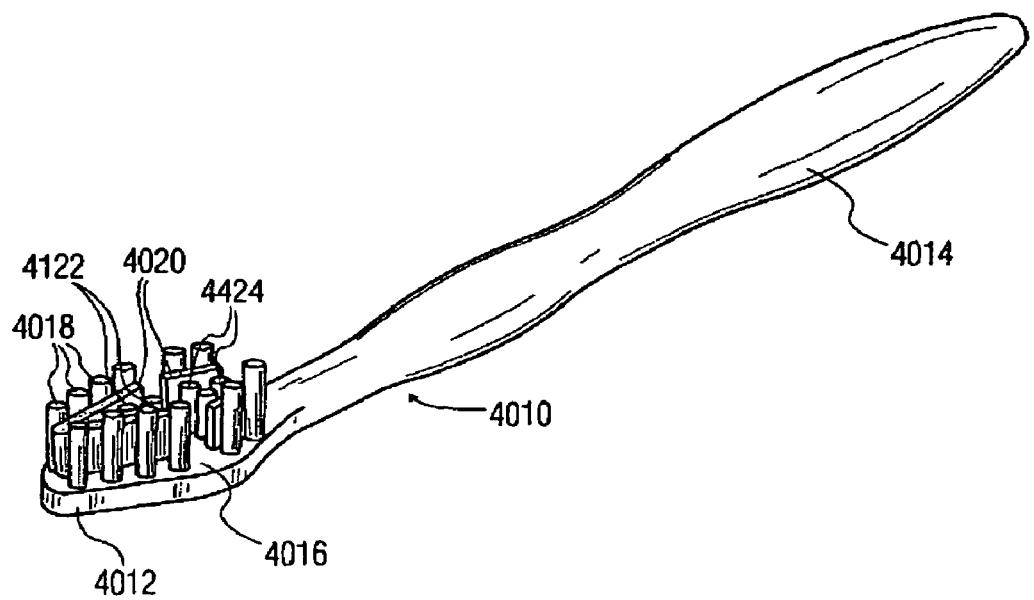

FIG. 44 is a perspective view of a fifth and alternative embodiment of the toothbrush shown in FIG. 40, wherein there a additional bristle tufts located central to the toothbrush head.

DETAILED DESCRIPTION OF ILLUSTRATIVE PREFERRED EMBODIMENTS OF THE INVENTION

A toothbrush is provided with a mechanical vibratory element and a head having a plurality of different types of cleaning/treating elements and cleaning areas which provide for an enhanced cleaning and/or treating effects. The cleaning/treating elements move by the mechanical vibratory device and/or independently of the mechanical vibratory device. Such a toothbrush, therefore, provides for synergistic and enhanced cleaning, scrubbing and massaging experience on the teeth and gums.

This application also discloses a toothbrush having multiple groupings of cleaning/treating elements uniquely mounted to the head of a toothbrush, which mounting facilitates flexible orientation of those groupings relative to the teeth and gums being cleaned. For example, the head of the subject toothbrush is designed to "wrap around" individual teeth resulting in deeper penetration of cleaning/treating elements between teeth. This overall cleaning is accomplished, for example, by independent movement of at least two groups of cleaning/treating elements relative to the toothbrush head and each other. The first group is a central grouping or "island" of cleaning/treating elements flexibly mounted to the toothbrush head.

The second group is preferably fixedly mounted to the toothbrush head in a configuration surrounding at least part of the central grouping. The central group is attached to the toothbrush head via a flexible elastomeric membrane, resilient plastic straps, webbing or other material that flexibly interconnects the first group with the toothbrush head.

In a preferred embodiment, the toothbrush head is divided into a plurality of separate cleaning areas. These areas include at least one and preferably two areas wherein the cleaning/treating elements are mounted to a base with other areas having the cleaning/treating elements mounted to pods wherein the pods have a greater degree of movability than do the bases. The pods are resilient so that during use, the cleaning/treating elements could be moved from their initial position and then returned to the initial position.

The pods may be formed from a narrow or small diameter beam extending from the body of the toothbrush head to a cleaning/treating elements support pad. Preferably the narrow or small diameter beam is enclosed in elastic material.

In a preferred practice of the invention, a relatively non-movable base is located at each of the distal and proximal ends of the toothbrush head with at least two elastic pods mounted between the two bases. These various cleaning areas are separated from each other by channels extending completely across the head in a transverse direction.

This application further discloses a toothbrush having multiple groupings of cleaning/treating elements ("islands") uniquely mounted to the head of a toothbrush, which mounting facilitates flexible orientation of those groupings relative to the teeth and gums being cleaned. More particularly, the bunches of cleaning/treating elements are mounted relative to the toothbrush head using a transverse, flexible membrane or web extending from the periphery of the cleaning/treating elements to the sidewalls of the toothbrush head.

This flexible mounting facilitates 360 degree limited angle wobble of the cleaning/treating elements. That, in turn, orients the cleaning/treating elements towards the teeth even if the toothbrush head is not angled directly parallel to the user's teeth.

The toothbrush of this invention includes a head in the form of a base having an upstanding wall to create a peripheral frame. In one embodiment, a thin resilient membrane or web is mounted within the frame. The membrane or web is capable of flexing to facilitate orientation of the cleaning/treating elements carried by the membrane relative to the teeth of the user.

Preferably, the cleaning/treating elements are bristles secured to the membrane or web by in-molded technology.

Additional cleaning/treating elements can be arranged on the periphery of the "islands" to facilitate cleaning in those areas between the "islands". In a preferred embodiment, these additional cleaning/treating elements are fixedly mounted to the toothbrush head outside the periphery of the membrane or web flexibly holding the "islands" of cleaning/treating elements. This combination of flexible and fixed mounting of cleaning/treating elements provides very effective brushing of teeth and massaging of gums.

Preferably, the toothbrush has a power source. The power source may be at least one battery, for example, 1, 2 or more batteries. The battery may be removable or fixed, rechargeable, non-rechargeable or rechargeable from an external source. Further, the battery may be of any size, such as, for example, AA, AAA, 9V and C. Alternatively, the power source may from an external source, for example via an AC adapter.

In use, for example, pressure applied to the toothbrush handle by a user causes a first group of cleaning/treating elements to contact the teeth being cleaned. As the force applied to the toothbrush exceeds a predetermined volume, a central group of cleaning/treating elements moves relative to the balance of the head. This movement, in turn, allows an outer group of fixed cleaning/treating elements to contact other areas of the teeth located at a greater distance from the head, including interproximal spaces between teeth.

This desired flexibility of the central grouping of cleaning/treating elements may be accomplished with an elastomeric bridge between the central movable group of cleaning/treating elements and the surrounding outer group of cleaning/treating elements. This elastomeric bridge may be continuous or may be a series of independent bridges with a void between each bridge to encourage greater flexibility. The width of this bridge can be adjusted to vary the amount of force needed to push the central group of cleaning/treating elements into a position where the outer group can achieve their greatest cleaning potential.

In another embodiment of this invention, the gap between the groups of cleaning/treating elements corresponding to the width of the elastomeric bridge between them can effectively be filled with elastomeric wipers that move as force is applied to the central group of cleaning/treating elements. For example, tapered elastomeric wipers can be mounted to the elastomeric bridge so that the narrower tip of the wipers flex inward and outward as force is applied to and released from the toothbrush handle. This wiping action further enhances the cleaning and treating functions of the disclosed toothbrush.

Turning to the Figures, both the toothbrush illustrated in FIG. 1 and that according to FIGS. 2 and 3 each have a handle 1, a front bristle-carrying head part 3 and a neck part 4, which connects the head part 3 to the handle 1. The bristles combined to form clusters of bristles 6 are anchored in a bristle carrier 5 and form a profiled brushing surface with their free ends. In the embodiment illustrated, the bristle carrier 5 with the clusters of bristles 6 is positioned, in a manner which is known per se and thus is not described in detail, on a retaining part 2 of the head part 3 such that it can be exchanged.

The neck part 4 is provided with neck-part zones 7 which are preferably made of an elastically relatively compliant material component and provide for, or additionally increase, the elasticity of the neck part 4, with the result that, during use of the toothbrush, the bristle-carrying head part 3 can be forced back resiliently in the case of forces acting in the direction of the brushing surface. Optionally, the neck-part zones 7 are designed as notches which extend over part of the neck circumference and are filled with elastically compliant material (e.g. with thermoplastic elastomer). It is understood that the form and number of neck-part zones can be different. It is also conceivable to have a flexible neck zone without using elastic material components, e.g. by providing constrictions or by way of a bellows.

Integrated in the front head part 3, or in that region of the neck part 4 which is adjacent to the head part 3, is a mechanical vibratory device 10, by means of which vibrations which effect or enhance the teeth-cleaning action may be imparted to the bristle-carrying head part 3. The vibratory device 10 can be connected to an electric power source, accommodated in the handle 1, via electrical connections running in the neck part 4, as is described herein below. In one embodiment, neck-part zones 7 are made of an elastically compliant material which dampens the vibration between the vibrating head part 3 and the handle 1, with the result that the vibratory action is produced, in particular, in the head part and is transmitted to the handle 1 to a slight extent. This means that slight vibrations can be felt in the handle 1 during the teeth-cleaning operation, and the toothbrush is thus comfortable to handle. In another embodiment, the vibration produced is not damped by the handle 1 and can act to full effect in the head part 3. Instead of the neck-part zones 7 having elastically compliant material, however, other vibration-damping elements could also be used. Further, the dampening may also be achieved, for example, by using a basic material, by the neck part being configured in a particular form, for example by the presence of a bellows/accordion part, etc.

Accommodated in the handle 1 is a sheath or sleeve 20 which extends in the longitudinal direction of said handle and is made of electrically conductive material. Both the handle 1 and the sleeve 20 are open to the rear, this forming a cavity 21 which can be closed from the rear by a closure part 22 and into which it is possible to insert a battery 25, in the preferred embodiment illustrated a commercially available, non-rechargeable cylindrical battery, with a defined power (e.g. 1.5 V) as the power source for the vibratory device 10. It would also be possible, however, for a button cell or for a rechargeable storage battery to be used as the power source.

A spring contact 29 for the positive pole 30 of the battery 25 (see FIG. 2) is fitted in the sleeve 20, on a transverse wall 28, and is connected to the vibratory device 10 via an electric line 31, a switch 32, which is installed in the sleeve 20 and can be actuated from the outside of the handle 1, and an electric line 33 running in the neck part 4. The electrical connection can be interrupted by means of the switch 32.

The closure part 22 is provided with a threaded stub 22a made of an electrically conductive material and can be screwed into the handle 1 and/or into the sleeve 20 by way of said threaded stub. The threaded stub 22a is provided with a contact surface 22b which, with the closure part 22 screwed in, comes into abutment against the negative pole 35 of the battery 25 inserted into the sleeve 20. The negative pole 35 is electrically connected to the vibratory device 10 via the threaded stub 22a, the sleeve 20 itself and a line 34, which connects the sleeve 20 to the vibratory device 10 and runs in the neck part 4.

Instead of being transmitted via the electrically conductive sleeve 20, it would also be possible for the power to be transmitted in some other way, for example using wires or an electrically conductive plastic.

In the exemplary embodiment illustrated in FIG. 1, the vibratory device 10 comprises a vibratory element 11' which functions preferably in the manner of a vibratory armature, can be electrically connected directly to the power source via the lines 33, 34 and, with the power source connected, is made to vibrate.

In the case of the toothbrush variant illustrated in FIGS. 2 and 3, the vibratory device 10 comprises a vibratory element 11 in the form of an eccentric, which produces mechanical vibrations and can be rotated about an axis located in the longitudinal direction of the toothbrush, and also comprises a drive which is arranged directly adjacent and is designed as a micromotor 15. The vibratory element 11 is connected to the shaft 15a of the micromotor 15, which can be electrically connected to the power source via the lines 33, 34. The micromotor 15 and the eccentric may be accommodated as a structural unit in a housing 12.

Instead of an eccentric which can be driven in rotation, it would also be possible to have a vibratory element 11 which can be driven in a translatory manner.

It would be possible, in the case of the toothbrush according to the invention, to arrange the bristle-carrying head part 3 such that it can be moved in relation to the neck part 4 in order for the latter, in the case of vibrations produced by means of the vibratory device 10, to be made to move in relation to the rest of the toothbrush.

The electric lines 31, 33, 34 could also be realized by electricity-conducting plastic tracks.

The switch 32, which connects or interrupts the lines 31, 33, may also be, for example, a magnetic switch.

The preferred configuration of the switch 32, however, has a pulse switch arranged on a printed circuit board as well as further electronic components which store the switching state.

It is also possible, however, for the electrical connection between the battery 25 and the vibratory element 11' (FIG. 1) or the drive 15 (FIGS. 2 and 3) to be produced or interrupted not by the switch 32, but by the closure part 22, which can be screwed into the handle 1 and/or into the sleeve 20 or connected to the same in a bayonet-like manner, being turned (i.e. the switch 32 is dispensed with in the case of such a configuration).

Instead of the rear closure part 22 being screwed to the handle 1, it would, of course, also be possible to have some other type of releasable connection (e.g. plug-in connection, bayonet connection, etc.) and a corresponding configuration of the contact part interacting with the negative pole 35.

It would also be possible for the closure part 22 to be in a form which is quite different to that illustrated in the drawing. For example, the closure part could be provided with a set-down surface or a foot part and thus serve as an element on which the toothbrush can be set down.

The toothbrush illustrated in FIG. 4 corresponds essentially to that according to FIGS. 2 and 3. According to FIG. 4, the vibratory device 10 is arranged directly in the front head part 3. In this exemplary embodiment, the sleeve 20 is dispensed with; the battery 25 is connected directly to the vibratory device 10 via the lines 33, 34. It is also the case with this toothbrush that use is preferably made of an exchangeable bristle carrier 5 which can be positioned on a retaining part 2 of the head part 3, e.g. in the manner of a snap-in connection. The capacity for changing the bristle carrier 5 provided with the clusters of bristles 6 is particularly advantageous since the toothbrush provided with the vibratory device 10 can be used irrespective of the service life of the bristles, which is usually even shorter than the service life of the battery 25.

As can be seen from FIG. 5, it is possible, instead of the bristle carrier 5 or 5a, which forms part of a conventional brush head and is provided with respective clusters of bristles 6 or 6a, to position other, optionally different bristle carriers or adapters 5b to 5d on the retaining part 2, these being provided with different interdental brushes 6b, 6c or interdental treatment parts 6d for effective cleaning of the spaces between the teeth. The interdental brush 6b may be designed, for example, as a helical brush made of coated wire with plastic filaments twisted in. The interdental brush 6c comprises bristles which, together, form a cluster tip. The treatment part 6d may be designed, for example, as a plastic element which has a tip and may preferably be provided with an abrasive coating for removing plaque and tartar from the spaces between the teeth. Of course, it would also be possible to use any other desired treatment heads. It is also the case with the variant according to FIGS. 4 and 5 that the bristle carrier 5 could be configured such that a vibration-induced movement in relation to the retaining part 2 were possible.

For the introduction of the vibratory device 10, the connecting lines 33, 34 and further electronic components, it is possible for the toothbrush according to the invention, or the housing thereof, to be produced in two parts and for the two parts to be welded in a water-tight manner once the abovementioned parts have been positioned therein. It is also possible, however, for the toothbrush according to the invention to be produced by injection molding preferably involving two or more components. The abovementioned parts are advantageously positioned as a unit in an injection molding made of a first material component and then encapsulated in the second material component (or in the further material component) by injection molding. It is not necessary here for full encapsulation to take place. Certain parts may be exposed, as a result of which it is possible to achieve an esthetic effect.

It would also be possible, however, for the abovementioned electronic components to be inserted into a ready-molded handle 1. In a preferred embodiment, since it is not only the vibratory element 11, 11' itself but also the drive, i.e. the micromotor 15, which are arranged in the front head part 3, or in the directly adjacent front region of the neck part 4, it is not necessary for a mechanical drive element to be led through the flexible neck part 4 in order to connect the micromotor to the vibratory element 11. In this embodiment, electric lines 33, 34 (e.g., wires, cables or electrically conductive plastic tracks) run through the neck part 4.

According to one embodiment of the invention, use is made of a mechanical vibratory device 10 which has a diameter of less than about 15 mm, preferably less than about 6 mm, and is less than about 35 mm, preferably less than about 20 mm, in length. This ensures that the toothbrush may be of ergonomic configuration and is easy to handle. The toothbrush according to the invention corresponds, in size, more or less to the conventional manual toothbrushes, which makes them more straightforward to handle in comparison with the commercially available, considerably larger electric toothbrushes.

A number of head configurations can produce an enhanced cleaning effect when the mechanical vibratory device is engaged.

FIGS. 6-9 illustrate a toothbrush 610 in accordance with one embodiment of this invention. As shown therein toothbrush 610 includes an elongated hand-held handle 612 with a head 614 connected to and extending from the handle. The head 614 is divided into a plurality of separate cleaning areas which are spaced from each other. As illustrated the cleaning areas include a base 616, 816 located at the distal end of the head 614 and projecting outwardly from the main body portion 930 of the head. Base 616, 816 includes at least one and preferably a plurality of cleaning/treating elements 618, 818. Head 614 further includes a base or supporting member 620, 820 at the proximal end of head 614. cleaning/treating elements 618, 818 also extend outwardly from base 620, 820.

Mounted between the cleaning areas which incorporate bases 616, 816 and 620, 820 are a pair of pods 622, 822, 624, 824. Each pod is provided with at least one and preferably a plurality of cleaning/treating elements 826. As later described the pods 622, 822, 624, 824 have a greater degree of movability than do the bases 616, 816, 620, 820. In the preferred practice of the invention the pods 622, 822, 624, 824 are resilient members so that the pod cleaning/treating elements add a motion range beyond the cleaning/treating elements 618, 818 which are generally static or non-movable. Preferably, because the various cleaning/treating elements are separated from each other such as by channels 728, 928 which extend completely across head 614 in a transverse direction and because of the elastic nature of pods 622, 822, 624, 824, the cleaning/treating elements 626, 826 are capable of 360 degrees rotation about the vertical axis of each individual pod. The angle of the bend is dictated by the ability of the material to bend.

Toothbrush 610 thus provides a head 614 wherein the front (distal end) and the back (proximal end) areas are in a relatively fixed position and wherein the cleaning/treating elements, such as bristle strands, 618, 818 do not have any extra degree of motion. The middle portion of head 614, however, has two areas of cleaning/treating elements 626, 826 which are capable of 360 degree rotation.

As best shown in FIG. 9 the head 914 includes a main body portion 930 which supports the bases and pods. Body portion 930 and bases 616 and 620 are preferably made from conventional hard plastic materials, such as polypropylene, commonly used in the making of toothbrush handles and heads. Pods 622, 822, 624, 824, however, are made so as to be resilient. In the preferred practice of this invention, the resiliency of pods 622, 822, 624, 824 is achieved by providing a thin diameter beam 932 which extends from the main body portion 930 of the head of the toothbrush. Beam 932 is joined into the bottom of a thin pad or plate 934 which provides a support area onto which the cleaning/treating elements 626, 826 are affixed. The manner of mounting the cleaning/treating elements 626, 826 to the support pads 934 can be achieved utilizing various cleaning/treating elements, such as bristles and other cleaning materials, in known attachment methods.

The desired flexibility or resiliency of the pods 622, 822, 624, 824 is enhanced by enclosing the thin beams 932 in elastic material 636, 826, 936 which could be acquired during the multi-injection molding process. The elastic material 636, 836, 936 serves as a rubber band by returning the beams 932 to their original form or initial position. This return action creates an active motion in the opposite direction of the beam bend which aids in the cleaning of teeth by introducing extra brushing strokes.

As best shown in FIGS. 6,7 and 9 the pods 622, 822, 624, 824 include a widened portion disposed toward the body 930. The support pads 934 are also widened. Each pod has a narrow or reduced diameter central portion 938 longitudinally intermediate the length of each pod. Thus, each pod is of generally mushroom shape.

Beam 932 could be of any suitable shape such as having a cross-section which is circular, square or any other geometric shape that provides a thin dimension or thin diameter to the beam to facilitate the bendability of the beam. The elastomer 636, 836, 936 may be considered as a continuous layer of any suitable thickness which covers the entire central area of head 614, 914 as illustrated so that both pods 622, 822, 624, 824 are incorporated as part of the same elastic material. The portion of the head 614, 914 which includes pods 622, 822, 624, 824 may be formed as a separate subassembly similar to the subassembly later described with respect to FIGS. 10 and 11.

Although the invention could be practiced with a single base and a single pod and could be practiced with the base having some, but a lesser degree of flexibility than the pod, the invention is preferably practiced wherein the base is generally static or non-movable. In addition, the invention is preferably practiced where there are a plurality of such bases and a plurality of pods. The drawings illustrate a preferred practice of the invention where there are a total of four separate cleaning areas with the pods being located in the central portion of head 614, 914. The invention is also preferably practiced where the cleaning/treating elements comprise a plurality of bristles or strands on each base and each pod.

As illustrated in FIG. 8 each base 816 and 820 and each pod 822 and 824 has a generally oval outer surface. The bases and pods are longitudinally aligned, but spaced from each other by the depressions or open areas which form the channels 728, 928. As also illustrated in FIG. 8 the pods have a larger outer surface or cleaning/treating element carrying surface than do the bases.

As shown in FIG. 7 the terminal surfaces of the cleaning/treating elements 618 and 626 are tapered so that the terminal surfaces of the cleaning/treating elements 618 taper outwardly in a direction toward the center of head 614 while the terminal surfaces of cleaning/treating elements 626 taper outwardly in a direction away from the center of head 614. Thus, the highest points of each set of cleaning/treating elements 618 and its adjacent set of cleaning/treating elements 626 are generally disposed toward each other for each pair of base and pod 616, 622 and 620, 624.

Any suitable form of cleaning/treating elements may be used as the cleaning/treating elements 618 and 626 in the broad practice of this invention. The term "cleaning/treating elements" is intended to be used in a generic sense which could include conventional fiber bristles or massage elements or other forms of cleaning/treating elements such as elastomeric fingers or walls arranged in a circular cross-sectional shape or any type of desired shape including straight portions or sinusoidal portions. Where bristles are used, the bristles could be mounted to tuft blocks or sections by extending through suitable openings in the tuft blocks so that the base of the bristles is mounted within or below the tuft block.

Using different cleaning materials as cleaning/treating elements of the toothbrushes may yield different effects. In an attempt to provide better stain removal a rubber-like material or elastomer can be used in combination with conventional bristles or used by itself to "brighten/whiten" the teeth.

It is to be understood that the specific illustration of the cleaning/treating elements is merely for exemplary purposes. The invention can be practiced with various combinations of the same or different cleaning/treating element configurations (such as stapled or in-molded technology bristles, etc.) and/or with the same bristle or cleaning/treating elements materials (such as nylon bristles, spiral bristles, rubber bristles, etc.) Similarly, while FIG. 7 illustrates the cleaning/treating elements to be generally perpendicular to the outer surface of head 614, some or all of the cleaning/treating elements may be angled at various angles with respect to the outer surface of head 614. It is thereby possible to select the combination of cleaning/treating element configurations, materials and orientations to achieve specific intended results to deliver additional oral health benefits, like enhanced cleaning tooth polishing, tooth whitening and/or massaging of the gums.

FIGS. 10-11 illustrate a further embodiment of this invention. The toothbrush 1110A has the ability to provide flexible support for the bristles 1026A, 1126A in designated areas. The flexibility is provided by designing the tuft holding areas 1034A, 1134A as plates which in combination with the stems 1038A, 1138A forms pods of mushroom shape. The mushroom stem 1038A, 1138A is made flexible to allow the plate 1034A, 1134A populated with bristles or cleaning/treating elements 1026A, 1126A to move in different directions while brushing, as described with respect to the flexible pods of FIGS. 6-9.

FIGS. 10-11 show the toothbrush 1110A and in particular the cleaning/treating element or bristle carrying portion 1023, 1133 of the head 1114A. As shown in FIG. 10 the bristle or cleaning/treating element carrying portion 1023 forms an initial subassembly. This subassembly is made by introducing the cleaning/treating elements 1026A into the mold cavity into which a plastic material is injected. As the material injected cools off it permanently traps the bristles or cleaning/treating elements 1026A to form a brush or subassembly 1023.

To achieve a functional flexibility and proper tuft retention the portion of the bristle holding part or subassembly 1023 which comprises the plates 1034A, stems 1038A and interconnecting support 1025, 1125 is preferably a blend of polypropylene (PP) and soft TPE. Once the PP/TPE blend is combined with the bristles 1026A the subassembly 1023 is formed. The subassembly 1023 is then overmolded with an entire toothbrush handle 1112A and head 1114A during a second injection cycle to form the completed toothbrush 1110A shown in FIG. 11. If desired or required the entire handle 1112A and head 1114A absent the subassembly 1123 could be made first and the subassembly or bristle retaining portion 1123 made second.

It is to be understood that the invention described in FIGS. 10-11 could be practiced where all portions of the head 1114 include the flexible mushroom sections without having less flexible base portions such as bases 616, 816 and 620, 820 of FIGS. 6-9. Similarly, the subassembly two shot techniques of FIGS. 10-11 could be utilized in the embodiment of FIGS. 5-9 for forming the two or more central pods as a single subassembly initially made separate from the remainder of the toothbrush head 1114. The final toothbrush would be made in a second injection molding process wherein the subassembly having interconnected pods 622, 822, 624, 824 would be molded to the handle 612, 812, 1112 and head 614, 914, 1114 made of more rigid material.

As noted, FIG. 7 illustrates the terminal surfaces of the cleaning/treating elements 618 and 626 to be tapered in an up and down or zig zag manner. FIGS. 10-11 show an alternative taper wherein the terminal surfaces form a smooth, gentle, concave shape. If desired, other shapes may be used such as a planar shape for the terminal surfaces or a convex shape as well as the zig zag or up and down shape shown in FIG. 7. Similarly, the terminal ends of the cleaning/treating elements in the FIGS. 6-9 embodiment, as well as those of FIGS. 10-11, could have the various shapes such as zig-zag, convex, concave or planar.

FIG. 12 illustrates a toothbrush 1210B which includes a power driven movable disc or section 1240 having cleaning elements. Although FIG. 12 shows movable section 1240 to be at the distal end of the head, the movable section(s) could be located at any desired location on the head.

FIGS. 13-16 illustrates head 1314-1614 of a manual toothbrush 1310 in accordance with one embodiment of this invention. Head 1314 is attached to handle 1312 (partially shown in FIG. 13). In one embodiment, two groups of cleaning/treating elements or bristles are arranged on head 1314-1614. The first group as illustrated in FIG. 13 is located in the central region of the head 1314 and comprises cleaning/treating elements 1318 in the form of strands or bristles.

The first group of cleaning elements 1318, 1418, 1518 is preferably mounted in a central movable portion 1417, 1517 of head 1314, 1414, 1514 that may be deflected downward in the direction of the arrow shown in FIG. 15 when a certain force is applied to the toothbrush handle. This movement of the central portion 1417, 1517 of head 1514 is facilitated by the flexible attachment of central portion 1417, 1517 to the balance of the head by elastomeric or other flexible material 1320, 1420, 1520. The elastomeric material 1320, 1420, 1520 bridges the gap between the central movable portion 1417, 1517 of head 1314, 1414, 1514 and the rigid portion 1415, 1515 of the head as illustrated in FIGS. 14 and 15.

Elastomeric material 1320, 1420, 1520 is preferably of a material or combinations of material that can flex to become altered from its original shape and recover to its original shape randomly during brushing.

The first group of cleaning/treating elements 1318, 1418, 1518 flexibly mounted in head 1314-1614 are complemented by a second group of fixed cleaning/treating elements 1322, 1422, 1522 generally arrayed in a surrounding relationship with the first group 1318, 1418, 1518.

The first and second group of cleaning/treating elements work together to provide improved cleansing of teeth. As illustrated in FIGS. 14 and 15 when minimal force is applied to toothbrush 1310 the end of the central group of cleaning elements 1418, 1518 facing the toothbrush user extend approximately the same distance from head 1414, 1514 as the outer or fixed group of cleansing elements 1422, 1522. When additional force is applied to the toothbrush, the center moveable portion 1517 of head 1514 slightly displaces downward (see FIG. 15). This facilitates deeper penetration of the second group of cleaning elements 1422, 1522 into the interproximal areas between teeth where plaque and food deposits can cause decay.

To further promote teeth cleaning, the toothbrush 1310 of this invention may include, for example, wipers 1324 positioned between the two groups of cleaning/treating elements as best illustrated in FIG. 13. These wipers are preferably made of rubber or like material with a typical cross-section as illustrated in FIGS. 14 and 15. These wipers 1324, 1424, 1524 extend radially from head 1314, 1414, 1514 and are preferably mounted on the flexible elastomeric material 1320, 1420, 1520 that bridges the gap between the first 1318, 1418, 1518 and second 1322, 1422, 1522 groups of cleaning elements. The outer ends 1325, 1425, 1525 of wiper 1324, 1424, 1524 will move inward toward each other upon application of force to the toothbrush due to the downward displacement of the movable portion 1417, 1517 of head 1314, 1414, 1514. As illustrated in FIG. 15 this downward displacement of movable portion 1517 of head 1514 causes the outer ends 1525 of wipers 1524 to sweep across the teeth thereby further enhancing the cleansing action of toothbrush 1310. Upon reduction of force on the toothbrush the movable portion 1517 of head 1514 moves back to its normal position, causing the ends 1525 of wipers 1524 to rotate back across the teeth. The extent of the sweeping motion of ends 1525 of wipers 1524 can be controlled by the location of the wipers relative to the placement of the elastomeric material 1520 between the two groups of cleaning elements. Further, any suitable form of cleaning/treating elements may be used as the cleaning/treating elements 1318 and 1322 in the broad practice of this invention.

It is to be understood that the specific illustration of the cleaning/treating elements is merely for exemplary purposes. The invention can be practiced with various combinations of the same or different cleaning/treating element configurations (such as stapled or in-molded technology bristles, etc.) and/or with the same bristle or cleaning/treating element materials (such as nylon bristles, spiral bristles, rubber bristles, etc.) Similarly, while FIGS. 13-15 illustrates the cleaning/treating elements to be generally perpendicular to head 1314, 1414, 1514 some or all of the cleaning/treating elements may be angled at various angles with respect to the outer surface of head 1314, 1414, 1514. It is thereby possible to select the combination of cleaning element configurations, materials and orientations to achieve specific intended results to deliver additional oral health benefits, like enhanced cleaning, tooth polishing, tooth whitening and/or massaging of the gums.

This invention may also be practiced where head 1314, 1414, 1514 includes one or more power or electrically operated movable sections carrying cleaning/treating elements.

FIG. 16 illustrates a toothbrush 1610A which includes a power driven movable disc or section 1650 having cleaning/treating elements. The movable section 1650 could be oscillated rotationally such as by using the type of drive mechanism shown in U.S. Pat. No. 5,625,916, or could move in and out using the type of drive mechanism shown in U.S. Pat. No. Re35,941; all of the details of both patents are incorporated herein by reference thereto. Alternatively, the other types of drives referred to above could move section 50 in other manners and directions. Although FIG. 16 shows movable section 1650 to be at one end of the head, the movable section(s) could be located at any desired location on the head.

FIGS. 17 and 18 illustrate a toothbrush 1710 with a handle 1712 and head 1714, 1814. Mounted on or in head 1714, 1814 are fingers 1716, 1816, preferably having a tapered shape. As shown in FIG. 18 fingers 1816 are preferably arranged about the periphery of head 1814. That location materially assists the gum massaging effect of the finger movement contemplated by this invention. More particularly, when the longitudinal axis of toothbrush 1710 is perpendicular to the axis of teeth being brushed, as is typical with most users, the fingers 1716, 1816 are closest to the gumline.

The fingers 1716, 1816 are preferably flexible and soft to the touch. Accordingly they may be formed of a soft elastomeric material. The general shape of fingers 2616, 2716, 2816 mounted in heads 2614, 2714, 2814 is illustrated in FIGS. 26-28. As so illustrated they are tapered and comprise all elastomeric material 2620 (FIG. 26) or a set of bristles 2718, 2818 partially surrounded by elastomeric material 2720, 2820 (FIGS. 27 and 28). The elastomeric material preferably extend along the length of finger 2616, 2716, 2816 a sufficient distance to facilitate attachment of ribs as described in more detail below.

To facilitate the therapeutic movement of fingers 1716-3116 it is important that head 1714 of toothbrush 1710 be flexible and that fingers 1716-3116 be flexibly mounted in head 1714. FIG. 25 illustrates one form of flexible mounting of fingers in head 2514. In this embodiment the head 2514 has a box-like shape in cross section. At least the upper face 2522 of head 2514, and preferably the entirety of head 2514, is made of a flexible material so that the axes of fingers 2516 can move relative to the plane of toothbrush 1710. The fingers 2516 project from apertures 2526 in the flexible upper face 2522 of head 2514. Any rib and finger 2216, 2316, 2416 arrangement shown in FIGS. 22-24 can be molded into the toothbrush head 2214. This flexible mounting in a flexible portion 2222 of head 2214 assists in obtaining the desired lateral movement of fingers relative tote axes of toothbrush 1710. The role of ribs in obtaining that movement is explained below.

To facilitate the therapeutic movement of fingers 1716-3116 it is important that head 1714 of toothbrush 1710 be flexible and that fingers 1716-3116 be flexibly mounted in head 1714. FIG. 25 illustrates one form of flexible mounting of fingers in head 2514. In this embodiment the head 2514 has a box-like shape in cross section. At least the upper face 2522 of head 2514, and preferably the entirety of head 2514, is made of a flexible material so that the axes of fingers 2516 can move relative to the plane of toothbrush 1710. The fingers 2516 project from apertures 2526 in the flexible upper face 2522 of head 2514. Any rib and finger 2216, 2316, 2416 arrangement shown in FIGS. 22-24 can be molded into the toothbrush head 2214. This flexible mounting in a flexible portion 2222 of head 2214 assists in obtaining the desired lateral movement of fingers relative to the axes of toothbrush 1710. The role of ribs in obtaining that movement is explained below.

FIG. 29 illustrates a powered toothbrush 2910A containing the fingers 2916 of the invention mounted on a flexible head 2914 of the toothbrush. Cleaning elements 1817 are preferably mounted inboard of fingers 1816 as illustrated in FIG. 18. Although FIG. 29 shows movable section 2930 to be at the distal end of the head, the movable section(s) could be located at any desired location on the head.

Another manner of imparting movement to the fingers 3016, 3116 is illustrated in FIGS. 30 and 31. As illustrated, fingers 3016, 3116 are physically linked to a flexible face 3022A, 3122A of head 3014, 3114 by angled rib 3024, 3124. Rib 3024, 3124 can be integrally molded into head 3014, 3114 and finger 3016, 3116 during the manufacture of toothbrush 1710. It can also be formed of a more rigid (than elastomeric) material such as polypropylene in order to enhance lateral movement of fingers 3016, 3116. Flexible face 3022A, 3122A of head 3014, 3114 in this embodiment can be molded around frame members 3026, 3126 forming the outer periphery of head 3014, 3114. These frame members 3026, 3126 of head 3014, 3114 may be attached to handle 1712 of toothbrush 1710 in a known manner.

The role of ribs 1824-2124 and flexible head 1814-2114 in imparting lateral movement to fingers 1816 is illustrated in FIGS. 18-21. FIG. 18 illustrates the location of fingers 1816 and ribs 1824 (having ends 1828) along outer edges of flexible face 1822 of head 1814. Other groups of bristles or cleaning/treating elements 1817 are arranged inboard of fingers 1816 as illustrated in FIG. 18. Fingers 1816 on the outer edge of head 1614 are closest to the gum line when the user holds the toothbrush in a normal position, i.e., with the longitudinal axis perpendicular to the axis of the user's teeth. Ribs 1824 extend from the side of finger 1816 to the face 1822 of flexible head 1814. These ribs can have a triangular, trapezoidal or like shape that interconnect the finger 1816 to the face of flexible head 1814. This interconnection assures lateral movement of finger 1816 as the face 1822 deflects outward or inward along the longitudinal axis when in use as described below.

The lateral movement of finger 1916-2116 is illustrated in the sequence shown in FIGS. 19-21. In FIG. 19 there is no deflection of face 1922 or rib 1924 of flexible head 1914. FIG. 20 represents a deflection of face 2022 that stretches that face as shown by the arrows 2023 at the edge of this fragmental view. When so stretched the ends 2028, 2128 of rib 2024 anchored to face 2022 move away from each other. That movement exerts a lateral force on finger 2016 causing it to move laterally toward the outside periphery of head 2014 as indicated by the arrow 2025 in FIG. 20. Conversely, when deflection (arrows 2123) of face 2122 of head 2114 causes that face to compress, the ribs 2124 push finger 2116 laterally in the opposite direction as indicated by the arrow 2125 in FIG. 21. Thus, as various forces are transmitted to flexible face 2122 or 2122A of head 2114 during use, that head moves in compression or expansion. That movement causes fingers 2116 to move in a lateral direction thereby promoting tooth cleaning and gum stimulation.

Another embodiment of the invention illustrated in FIGS. 30 and 31 shows ribs 3024, 3124 oriented approximately 90 degrees to the longitudinal axis of toothbrush 1710 versus approximately 45 degrees shown in FIGS. 18-21. In the former embodiment, movement of the flexible face 3022A in an upward direction (FIG. 30) causes lateral inward movement of fingers 3016 as illustrated by the arrows 3127 in this Figure. Conversely, downward movement of flexible face 3022A would cause lateral movement of fingers 3016 away from each other toward the outside of head 3014 (not illustrated).

Other arrangements of ribs 2224, 2324, 2424 (having ends 2228, 2328, 2428) and their attachment to fingers 2216, 2316, 2416 on faces 2222, 2322, 2422 are illustrated in FIGS. 22-24. As illustrated, multiple fingers 2216, 2316, 2416 are interconnected by a continuous rib 2224, 2324, 2424. FIG. 22 illustrates the interconnecting ribs 2224 on one side of fingers 2216. Thus, upon deflection of flexible face 2222 of head 2214 all fingers 2216 move in the same direction as indicated by the arrows 2229, 2329 in FIGS. 22 and 23. If it were desirable to have the fingers 2416 move in different directions the arrangement of ribs 2424 shown in FIG. 24 can be utilized.

It is to be understood that the specific illustration of the cleaning/treating elements is merely for exemplary purposes. The invention can be practiced with various combinations of the same or different cleaning/treating element configurations (such as stapled or in-molded technology bristles, etc.) and/or with the same bristle or cleaning/treating element materials (such as nylon bristles, spiral bristles, rubber bristles, etc.). Similarly, while FIG. 18 illustrates the cleaning/treating elements to be generally perpendicular to head 1814, some or all of the cleaning/treating elements may be angled at various angles with respect to the outer surface of head 1814. It is thereby possible to select the combination of cleaning/treating element configurations, materials and orientations to achieve specific intended results to deliver additional oral health benefits, like enhanced cleaning, tooth polishing, tooth whitening and/or massaging of the gums.

Referring to FIGS. 32 and 33, an exemplary toothbrush including a head plate according to the invention is illustrated and generally indicated at 3200. Toothbrush 3200 includes a handle 3202 at a proximal end thereof, and a brush section 3204 that is defined by a neck 3210 that terminates in a head 3220 at a distal end of toothbrush 3200. Handle 3202 has a free proximal end 3208 and an opposite neck end 3206. Neck 3210 generally includes a first end 3214 and a second end 3216 with first end 3214 being located at neck end 3206 of handle 3202 and the second end 3216 being located at head 3220. In other words, neck 3210 is the portion of toothbrush 3200 that extends between handle 3202 and head 3220. Head 3220 is preferably generally aligned with the longitudinal axis x-x of toothbrush 3200.

Neck 3210 and handle 3202 may be constructed as a unitary member by forming neck 3210 integral to handle 3202 at neck end 3206 of handle 3202, or may be formed detachable from handle 3202 at the neck end 3206. In accordance with this detachable embodiment, the combined neck 3210 and head 3220 can be removed from handle 3202 to permit cleaning, servicing and/or interchanging of either handle 3202 or the combined neck 3210 and head 3220 (brush section 3204). When neck 3210 is formed to be detachable from handle 3202, first neck end 3214 preferably includes a connector linkage (not shown) detachably joined to handle 3202 using traditional techniques. It will also be appreciated that the point of detachment may be between head 3220 and neck 3210 such that head 3220 is of a refill head type.

It will further be appreciated that the illustrated shapes of handle 3202 and neck 3210 are merely exemplary in nature and handle 3202 and/or neck 3210 can be formed to have any number of shapes. Preferably, the shapes of handle 3202 and neck 3210 are ergonomically pleasing to a user of toothbrush 3200 and provide a toothbrush that is easily gripped and held and easily manipulated by a user. For example, handle 3202 may include a slightly recessed finger section 3218 which is formed on handle 3202. The recessed finger section 3218 is designed to receive the thumb of one hand to thereby assist a user in proper placement of toothbrush 3200 in a user's hand. Recessed finger section 3218 may include ribs or another type of roughened surface to assist a user in gripping toothbrush 3200 at recessed finger sections 3218. Of course other patterns for providing recessed finger sections may be employed.

The head plate for the bristles is formed with a solid perimeter and defines a field of variously shaped and sized holes within this perimeter. Fibers that are to form the tufts are then placed in the holes in the field of the head plate, and the backs of the tufts are melted together to fix their position relative to one another.

The tufted head plate is then inserted into a predefined receiving portion of the head portion of a toothbrush handle and is sonically welded into place. The brush is then end rounded and packaged for sale as a traditional toothbrush.

As is shown in FIGS. 32 and 33 of the present invention, a head plate 3250 is provided, and is fixed to head 3220 of toothbrush 3200, preferably by sonic welding, although any other appropriate attachment technique may be employed. Head plate 3250 is formed of at least two materials. A first rigid material is used to form the perimeter portion 3252 of the head plate. Such a material, such as for example polypropylene, is easily sonically welded. A tuft field 3254 is formed of a flexible elastomer (preferably having a hardness of 90 Shore A or less).

A process known as "Anchor Free Tufting" (AFT) is used in the formation of head 3250. In such an AFT process, head plate 3250 is used for holding toothbrush bristles in their proper orientation. When the bristles are placed in their proper orientation through the corresponding holes in the head plate 3250, the head plate 3250 is placed in the head plate cavity formed in the front face of the head section 3204 of the brush, and for insertion into a toothbrush.

As is best shown in FIG. 32, head plate 3250 is formed with a solid perimeter and defines a field of variously shaped and sized apertures or holes 3256 within the flexible elastomer tuft field 3254. Fibers that are to form one or more bristle tufts 3258 are then placed in the holes in field 3254 of head plate 3250, and the backs of tufts 3258 are melted together to fix their position relative to one another. Thus, such a head plate is able to flex, thereby allowing the tuft field and bristles to move under normal brushing conditions, while providing a perimeter of structural rigidity that is able to be sonically welded. Therefore, the head plate and bristles move or flex under the pressure of normal brushing. While bristles 3258 are shown, elastomeric members may also be used in place of these tufts. Furthermore, while a particular tuft field pattern is shown, any desirable tuft field pattern may be employed. Furthermore, the bristle material need not be the same for all of the tufts, and indeed varying materials for performance color or indication of life remaining in the brush head, may be used exclusively, or in combination as desired.

FIG. 34 illustrates a toothbrush 3410 which could be of generally typical structure in the sense of having a handle 3412 at one end connected to a cleaning head 3414 which has an outer surface 3416 from which a plurality of cleaning/treating elements extend.

In a preferred embodiment, toothbrush 3410 includes a mechanical vibratory device as described above (not shown in FIG. 34) which causes the cleaning head to vibrate. The mechanical vibratory device is preferably located in the head or in a region adjacent to the cleaning head and operatively connected to an electric power source.

In accordance with this invention the cleaning head 3414, as shown in FIG. 35, includes a peripheral frame 3518. A resilient membrane 3520 is secured across frame 3518 so that membrane 3520 is free to move in a direction toward and away from the outer surface 3416. The membrane 3520 could be recessed below outer surface 3416 or could be flush with the outer surface. Because membrane 3416 is mounted across frame 3418 when pressure is applied to membrane 3520 the membrane would move in a direction away from the outer surface 3416 and would return in the opposite direction upon release or diminution of pressure.

Head 3414 may be completely open in the area of frame 3518, except for membrane 3520, or may include a rear wall spanning the frame and spaced from membrane 3520 to permit inward movement of membrane 3520.

An embodiment of the present invention is preferably directed toward making use of the movement that results from resilient membrane 3520 in combination with various specialized types of cleaning/treating elements, particularly such elements wherein some of the elements have physical characteristics which differ from other of the elements so that an enhanced cleaning or treatment results from the combination of the actual cleaning/treating elements performing their specialized functions and the movement of the resilient or flexible membrane 3520. Membrane 3520 may be considered as defining a cleaning field in which the various cleaning/treating elements are located.

FIG. 34 illustrates some examples of cleaning/treating elements wherein the various elements are in the form of different types of bristles. As illustrated, the cleaning/treating elements include angled bristles 3422, 3424 which may also be arranged to crisscross each other. Other bristles could include generally straight or inclined bristles having slanted or pointed ends, respectively, and other straight bristles 3428 having flat ends. The slanted end bristles 3426 have their outer surface taper from one side to another, while the pointed portion of the bristles 3430 is located at the center of the bristles. As shown in FIGS. 34 and 38 the various combinations of bristles could also result in multi-level bristles.

The bristles could be secured to membrane 3520 in any suitable manner such as by anchor-free tufting or by any other conventional techniques.

Instead of having individual tufts of bristles the bristles could be located closely together to form an elongated bristle wall 3832 such as shown in FIG. 38. Such bristle wall 3832 could be included on the same cleaning field as various of the previously described tufts of bristles. The wall 3832 could be straight, curved, sinusoidal or of any desired shape.

The invention may be practiced where the cleaning/treating elements are elastomeric elements rather than tufts of bristles of FIGS. 34 and 38 made of nylon fiber or the like. It is also contemplated that the invention maybe practiced where the cleaning/treating elements include a combination of bristle elements and non-bristle elements. The non-bristle elements include, for example, a tongue-cleaning structure, elastomeric fingers, elastomeric walls and prophy cups.

FIGS. 36-37 show some examples of the incorporation of elastomeric cleaning/treating elements. As shown in FIG. 36 a plurality of rubber or elastomeric fingers 3634 are mounted to membrane 3520. The fingers could be of any suitable size and shape such as being oval at their base and tapering uniformly inwardly toward their free end to generally end in a point or narrow line type structure at their free end. The size of the individual elastomeric fingers 3634 could vary as illustrated in FIG. 36. FIG. 37 shows other forms of elastomeric cleaning/treating elements. Such other forms include prophy cups 3736, elastomeric walls 3738 and elastomeric fingers 3740 which would be conically shaped to function as massage elements. The elastomeric walls could be straight, arcuate, sinusoidal or of any other desired shape. The size and number and location of these elastomeric elements could vary. FIG. 37 also shows the combination of elastomeric elements and bristles. As shown therein, various tufts of bristles 3742 are located in a ring-like pattern around a central portion of bristles 3744. It is to be understood that any combination of the bristles and/or elastomeric elements mounted to membrane 3520 could be used within the spirit of this invention. Similarly, as illustrated in FIG. 39, the frame 3518 of head 3414 could be of sufficient size so as to accommodate cleaning/treating elements such as spaced tufts of bristles 3946 secured directly to the rigid material such as conventionally used in the toothbrush head and handle. These fixed cleaning/treating elements 3946 would be in combination with the movable elements on the cleaning field formed by membrane 3520.

The toothbrush and particularly the cleaning head 3414 could also be provided with various forms of structure to achieve tongue cleaning. Thus, FIG. 38 illustrates tongue cleaning structure 3848 at the backside of head 3414 while FIG. 39 illustrates the tongue cleaning structure 3950 at the tip of cleaning head 2414 remote from the handle. The tongue cleaning structure could be stiff or flexible fingers or walls, made from a suitable elastomeric material.

The various cleaning/treating elements could also be located to provide for interproximal cleaning.

In the preferred practice of the invention the resilient membrane 3520 has mounted to it a plurality of various types of cleaning/treating elements with different physical characteristics. Such physical characteristics could be of the types previously described with regard to size, shape and structure of the cleaning/treating elements or could be the result of different internal characteristics such as differing degrees of stiffness.

The present invention thus makes it possible to select the combination of cleaning/treating element configurations, materials and orientations to achieve specific intended results to deliver additional oral health benefits such as enhanced cleaning, tooth polishing, tooth whitening and/or the massaging of gums. These results are enhanced by mounting the various cleaning/treating elements on the resilient cleaning field so that in addition to the benefits from the specific physical characteristics of the individual cleaning/treating elements there is also a movement imparted to the cleaning/treating elements when pressure is applied to the elements such as by contacting the teeth thereby causing the resilient membrane to move in response to the pressure.

Referring now to FIG. 40 of the drawings, the toothbrush 4010 of this invention includes a body formed of an elongated member with a head 4012 on one end and a handle 4014 on the other. The handle 4014 may be conventional in shape and forms no part of this invention. The head 4012 has an flattened bristle mounting surface or face 4016, from which extend a plurality of bristles having proximal ends attached to the face 4016 and distal ends extending outwardly from the head 4012. As seen in FIG. 40, there are two types of bristle groups, the first type being peripheral bristle tufts 4018, located about the periphery of the head 4012. These peripheral bristle tufts 4018 are generally symmetrical in cross-section, i.e. circular; square; or, if oval or rectangular, having a larger cross-sectional dimension less than about 1.3 times the shorter cross-sectional dimension. Further, these peripheral bristle tufts 4018 have a cross-sectional diameter or larger dimension of from about 1.0 mm to about 2.0 mm, preferably from 1.4 mm to about 1.9 mm, and more preferably from about 1.5 mm to about 1.7 mm. The second type of bristle group shown are bristle bars 4020, which are generally elongated in shape and which are located adjacent to the peripheral bristle tufts 4018 and internal to the head 4012 of the peripheral bristle tufts 4018. Bristle bars 4020 have a cross-sectional length of at least 2.5 mm, preferably at least 3.0 mm and more preferably at least 4 mm.

In a preferred embodiment, toothbrush 4010 includes a mechanical vibratory device as described above (not shown in FIG. 40) which causes the head to vibrate. The mechanical vibratory device is located in the head or in a region adjacent to the head and operatively connected to an electric power source. The bristle tufts and bristle bars are moved by the mechanical vibratory device and/or independently of the mechanical vibratory device in a manner so as to provide an enhanced scrubbing action of the teeth and gums.

As illustrated in FIGS. 40 and 41 the bristle bars 4020 of the present invention can be shaped in a variety of geometric forms, such as substantially parallelepipeds; or alternately having curved foot-prints to conform to the curvature of the toothbrush head 4012; or combinations thereof. The peripheral bristle tufts 4018 can preferably be taller, i.e. in height from the face 4016, than the bristle bars 4020 or any other bristle tufts on the toothbrush. Peripheral bristle tufts 4018 having such extra height over any other bristle tufts within the head 4012 will penetrate into the interproximal areas between teeth for enhanced cleaning therein without interference by such other shorter bristle tufts. It is preferred that the peripheral bristle tufts are from about 9.0 mm to about 13.0 mm in height about the face 4016 of the toothbrush, preferably from about 11 mm to about 12 mm in height. Further, the bristle bars 4020 are preferably at least about 50% to about 85% of the height of the peripheral bristle tufts 4018, so as to provide the desired support to the peripheral bristle tufts 4018.

U.S. Pat. No. 5,511,275 to Volpenhein discloses that in addition to the stiffness characteristics of the bristles, the more tightly bristles are packed together in tufts, the more additional support they will lend each other to enhance their overall stiffness and cleaning ability. Volpenhein further discloses as a measure of this effect a Buttress Factor defined as the cross-sectional area taken up by the bristles divided by the total cross sectional area of the tuft at its base, i.e. from 0 to 1. The higher the Buttress Factor, the greater the stiffness and cleaning ability of the bristles. While Volpenhein discloses toothbrushes having Buttress Factors of from 0.8 to 0.96, the bristle tufts 4018 and bristle bars 4020 in the present invention surprisingly only require a Buttress Factor of from about 0.6 to about 0.75. Preferably the Buttress Factor of both the bristle tufts 4018 and the bristle bars 4020 of the present invention is from about 0.65 to about 0.7, and most preferably about 0.68. This Buttress Factor range is further advantageous in equating closely with Du Pont Polymers' recommended optimum bristle wear performance packing factor range of 0.63 to 0.74, defined similarly as filament cross-sectional area divided by tuft hole opening. See, Du Pont Polymers, Wilmington, Del. 19898 publication Z-1737.

As shown in FIGS. 41, 42 and 43 the bristle bars 4020 may generally have rectangular, curved, or oval foot-prints. The general shape of the bristle bars 4020 is not critical, so long as the bristle bars are of sufficient dimension to provide the adjacent peripheral tufts support during tooth brushing. Considering the simultaneous brushing movement of toothbrushes from the front to the rear of the mouth and up and down; the bristle bars 4020 are preferably of such a length and such a spacing from the peripheral bristle tufts 4018, to provide support to each adjacent peripheral bristle tuft 4018 when the adjacent peripheral bristle tuft is deflected toward the particular bristle bar 4020 at any angle up to 20 degrees from the perpendicular therebetween, preferably up to 30 degrees, more preferably up to 40 degrees and most preferably up to 50 degrees or more.

The width of the bristle bars 4020, shown as dimension "a" in FIG. 40, is preferably at least about 1.0 mm, more preferably at least about 1.5 mm. Further, the narrowest transverse space between each peripheral tuft 4018 and the supporting bristle bar 4020 therefore, are preferably not greater than about 1.5 mm, more preferably not greater than 1.0 mm and most preferably not greater than about 0.7 mm.

Referring again to FIGS. 40 and 41, it can be seen that in each figure a transverse opening is provided between the bristle tufts 4018 and extending through the bristle bars 4020, toward the center of the head 4012; this opening being located middle way up the head 4012. This opening may be provided to enhance the users ability to clean the toothbrush of toothpaste and debris accumulated during brushing, by providing a clear channel for rinse water to the interior of the head 4012. Alternatively, additional openings can be provided as is illustrated in FIG. 42, to further enhance the ease of cleaning.

Another embodiment of the present invention, as illustrated in FIG. 43, has a head 4012 having extending from its face 4016 the same peripheral tufts 4018 and adjacent bristle bars 4020 internal thereto as the afore-described embodiment; however, in addition to these sets of bristle tufts 4018 and bars 4020, there is a set of additional bristle bars 4022 located central to the head ("central bristle bars"). These central bristle bars, illustrated as wedges in FIG. 43, provide not only additional bristle area for cleaning, but also, enhanced support for the now intermediate within the head located bristle bars 4020, to enhance the overall stiffness and cleaning ability of the toothbrush 4010. These central bristle bars 4022 may have cross-sections other than wedges, such as ovals, egg shapes, or rectangular.

An alternative embodiment of the present invention shown in FIG. 44 is similar to the second embodiment disclosed above, except the central bristle bars 4322 can be replaced by a plurality of central bristle tufts 4424, similar to the individual, peripheral bristle tufts 4018. The height of any such central bristle tufts 4024 above the brush face 4016 can be equal to or less than that of the now intermediate within the head located bristle bars 4020.

Various modifications and variations of the described compositions, materials and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art or in related fields are intended to be within the scope of the following claims.

What is claimed is:

1. A powered toothbrush comprising:
   a handle having a longitudinal axis;
   a cleaning head attached to said handle, the cleaning head having a main body formed of a substantially rigid material;
   a plurality of spaced apart beams protruding from the main body, the beams constructed of the substantially rigid material;
   the plurality of beams enclosed in a flexible elastic material, thereby forming a plurality of spaced apart support structures that are rotatably movable with respect to the main body;
   a cleaning/treating element attached to each of the support structures, further comprising at least two cleaning/treating elements extending from the main body that are non-movable with respect to the main body; and
   a power source, a motor, and a mechanical vibratory device which causes the cleaning head to vibrate;
   wherein the cleaning/treating elements attached to the support structures and the at least two cleaning/treating elements extending from the main body are aligned along the longitudinal axis of the handle, the cleaning/treating elements attached to the support structures located between the at least two extending from the main body;
   wherein the cleaning/treating elements attached to the support structures and the at least two cleaning/treating elements extend along the substantial entirety of the width of the head.

2. A powered toothbrush comprising a handle, a cleaning head attached to said handle and having a first end adjacent the handle and a free end, the cleaning head having a main body formed of a substantially rigid material, a power source, a motor, a mechanical vibratory device which causes the cleaning head to vibrate, the motor and the vibratory device disposed in the handle, wherein said cleaning head includes a first cleaning/treating element adjacent the first end that is non-movable relative to the main body and is the endmost cleaning/treating element at the first end, a second cleaning/treating element adjacent the free end that is non-movable relative to the main body and is the endmost cleaning/treating element at the free end, and a plurality of third cleaning/treating elements disposed between the first and second cleaning/treating elements, wherein each of said plurality of third cleaning/treating elements extends from one of a plurality of support structures having at least a portion that is rotatably movable relative to the cleaning head about a vertical axis extending upwardly from said one of a plurality of support structures, the vertical axis extending substantially perpendicular to a longitudinal axis of the handle, and wherein each of said plurality of third cleaning/treating elements is movable independent of any other third cleaning/treating element, and further comprising a plurality of channels, each of the channels extending transversely and substantially completely across a surface of the cleaning head from which the cleaning/treating elements extend and separating a support structure from one of an adjacent support structure, the free end or the first end; and each of the plurality of support structures comprising a beam of the substantially rigid material extending from the main body and enclosed in an elastic material.

3. The powered toothbrush according to claim 2, wherein the support structures enable angular movement of the third cleaning/treating elements relative to the cleaning head.

4. The powered toothbrush of claim 3, wherein the first and second cleaning/treating elements are bristle tufts.

5. The powered toothbrush of claim 4, wherein the plurality of third cleaning/treating elements disposed between the first and second cleaning/treating elements include bristle tufts.

6. The powered toothbrush of claim 5, wherein the motor is an electric motor.

7. The powered toothbrush of claim 6, wherein the power source is a battery.

8. The powered toothbrush of claim 7, wherein the cleaning head further comprises at least two cleaning/treating elements having different cross sections.

9. The powered toothbrush according to claim 2, wherein at least one of said cleaning/treating elements extends further from the cleaning head than at least one other of said cleaning/treating elements.

10. The powered toothbrush according to claim 2, wherein said second cleaning/treating element includes a tuft that follows at least a portion of a contour of the free end of the cleaning head.

11. The powered toothbrush of claim 2 wherein the substantially rigid material is a hard plastic.

12. The powered toothbrush of claim 11 wherein the hard plastic is polypropylene.

* * * * *